(12) United States Patent
de Groot et al.

(10) Patent No.: US 6,436,643 B1
(45) Date of Patent: Aug. 20, 2002

(54) PROCESS FOR SITE-DIRECTED INTEGRATION OF MULTIPLE COPIES OF A GENE IN A MOULD

(75) Inventors: Marcellus Johannes Augustinus de Groot; Alida Godelieve Maria Beijersbergen; Wouter Musters, all of Vlaardingen (NL)

(73) Assignee: Unilever Patent Holdings BV, Vlaardingen (NL)

( * ) Notice: Subject to any disclaimer, the term of this patent is extended or adjusted under 35 U.S.C. 154(b) by 0 days.

(21) Appl. No.: 09/581,941
(22) PCT Filed: Oct. 6, 1998
(86) PCT No.: PCT/EP98/06519
§ 371 (c)(1),
(2), (4) Date: Aug. 2, 2000
(87) PCT Pub. No.: WO99/32641
PCT Pub. Date: Jul. 1, 1999

(30) Foreign Application Priority Data

Dec. 22, 1997 (EP) ............................................. 97204062

(51) Int. Cl.⁷ .......................... C12Q 1/68; C12N 15/80; C12N 15/64; C12N 1/15
(52) U.S. Cl. ......................... 435/6; 435/69.1; 435/69.8; 435/455; 435/320.1; 435/471; 435/484; 435/477; 435/478; 435/254.11; 435/254.3; 435/254.4; 435/254.5; 435/254.6; 435/254.7; 435/254.8; 435/254.9; 536/23.1; 536/23.2; 536/23.7; 536/24.1
(58) Field of Search ............................... 435/455, 320.1, 435/471, 484, 477, 478, 254.11, 254.3, 254.4, 254.5, 254.6, 254.7, 254.8, 254.9, 6, 69.1, 69.8; 536/23.1, 23.2, 23.7, 24.1

(56) References Cited

FOREIGN PATENT DOCUMENTS

| | | |
|---|---|---|
| EP | 0 249 350 | 12/1987 |
| EP | 0 635 574 A1 | 1/1995 |
| EP | 0 778 348 A1 | 6/1997 |
| EP | 0 950 712 A1 | 10/1999 |
| WO | WO 91/00920 | 1/1991 |
| WO | WO 92/10577 | 6/1992 |
| WO | WO 98/07873 | 2/1998 |

OTHER PUBLICATIONS

Verdoes et al, Transgenic Research, 2:84–92 (1993).
Fowler et al, Molecular Microbiology, 9(5):989–998 (1993).
Verdoes et al, Journal of Biotechnology, 36:165–175 (1994).
Geisen et al, Curr Genet, 15:307–309 (1989).
Kelly et al, Curr Genet, 12:21–31 (1987).
Bussink et al, Appl. Microbiol. Biotechnol., 37:324–329 (1992).
van Gemeren et al, Appl. Microbiol. Biotechnol., 45:755–763 (1996).
Kubicek–Pranz et al, Journal of Biotechnology, 20:83–94 (1991).
Gouka et al, Curr Genet, 27:536–540 (1995).

Primary Examiner—David Guzo
(74) Attorney, Agent, or Firm—Morgan, Lewis & Bockius LLP

(57) ABSTRACT

A process for site-directed integration of multiple copies of a gene in a mould is provided, which comprises transforming a mould cell containing in its chromosomal DNA a restriction site for a rare-cutting endonuclease, e.g., I-SceI, preferably introduced at a desired locus, e.g., within a selectable marker gene or in the neighborhood thereof, with a piece of DNA comprising multiple copies of at least one expressible gene comprising at least one structural gene encoding a desired protein, surrounded by two DNA fragments homologous to part of the DNA upstream and downstream, and in the neighborhood, of said restriction site, while during the transformation of the mould the presence of the rare-cutting endonuclease is provided, followed by selecting or screening for a mould cell in which the multiple gene copies of said expressible gene are inserted into the chromosomal DNA of the mould. The piece of DNA can comprise a third DNA fragment completing any disrupted or partially deleted selectable marker gene in the chromosomal DNA. Preferably the mould belongs to the genus Aspergillus, especially to the species *Aspergillus awamori*. Also provided are a transformed mould obtainable by a process according to the invention, a process for culturing such transformed mould, and a process for producing and optionally secreting a desired protein by culturing such transformed mould under conditions whereby the structural gene encoding said desired protein is expressed, and optionally isolating or concentrating the desired protein.

18 Claims, 13 Drawing Sheets

EcoRI- NotI -"HindIII"

PROCESS FOR SITE-DIRECTED INTEGRATION OF MULTIPLE COPIES OF A GENE IN A MOULD

This application is the nation phase of international application PCT/EP98/06519 filed Oct. 6, 1998 which designated U.S.

The invention relates to a process for site-directed integration of multiple copies of a gene in a mould, to a transformed mould obtainable by such process, to a process for culturing such transformed mould, and to a process for producing and optionally secreting a desired protein by culturing such transformed mould. In particular, the invention provides a process for preparing a protein by a mould transformed by multicopy integration of at least one expressible gene comprising a structural gene encoding a desired protein into the genome of a mould, especially of moulds belonging to the genus Aspergillus.

In this specification the expression "expressible gene" means a structural gene encoding a protein, either homologous or heterologous to the host organism, in combination with DNA sequences for proper transcription and translation of the structural gene, and optionally with secretion signal DNA sequences, which DNA sequences should be functional in the host mould. Further, in this specification the expressions "mould" and "filamentous fungus" are considered as synonyms.

BACKGROUND OF THE INVENTION AND PRIOR ART

1. Filamentous fungi and especially species such as *Aspergillus awamori, Aspergillus niger, Trichoderma reesei* and *Fusarium graminearum* have shown to be attractive hosts for large scale production of homologous and heterologous proteins. They have the capacity to secrete substantial amounts of protein into the medium, large scale fermentation is generally well established and most of them they have a GRAS (Generally Recognized As Safe) status, which makes it possible to use these species in the food and food-processing industry. Moreover, the mould *Fusarium graminearum* A 3/5, the Quorn$^R$ myco-protein fungus, has also been used as a commercial human food source in the UK for over 10 years (Royer et al.; Bio/Technology 13 (1995) 1479–1483).

The production of fungal proteins, of either homologous or heterologous origin, by filamentous fungi is usually very efficient and production levels of grams per liter were reached. However, compared to this the production levels of heterologous proteins of mammalian, bacterial or plant origin in moulds are relatively low. In order to improve the production of both homologous and heterologous proteins several strategies have been developed. The basic strategy that is commonly applied to achieve higher protein production in moulds is the introduction of multiple copies of the gene encoding the desired protein.

2. Whereas moulds have been successfully used for the production of enzymes, antibody fragments and peptides at laboratory and commercial scale (xylanase, pectinase, etc), the acceptance of products from these genetically modified organisms (GMO) in the market has experienced some unexpected difficulties in the past few years.

(a) In general there is a growing concern about the use of antibiotic resistance genes in genetically modified organisms. The main reason for this concern is the possibility that such a gene might be transferred into and expressed in gut micro-organisms, which would thereby become antibiotic resistant ("Report on the use of antibiotic resistance markers in genetically modified food organisms" published by the Advisory Committee on Novel Foods and Processes, Ministry of Agriculture, Fisheries and Food, England, 1994).

(b) Further, the presence of other foreign DNA such as remnants of vector DNA used in cloning is also undesired.

(c) Another concern is the fact that in general the genetically modified strains contain randomly integrated genetic material. In the perception of some consumer organisations this would constitute an unpredictable safety risk, and could mean a barrier to the acceptation of derived products.

3. Therefore, the recombinant mould should ideally contain multiple copies of the gene encoding the desired protein integrated at only a predetermined locus in the genome and no other foreign DNA should be present in order to produce proteins in moulds in both an economically attractive manner and in a way that deals with the concerns about genetically modified organisms as described above.

The generation of mould strains that meet these criteria has not been reported in literature.

The commonly applied system for integration of single or multiple copies of a gene into the genome of moulds, e.g. Aspergillus, Trichoderma and *Fusarium graminearum* makes use of plasmids which in addition to the gene encoding a desired protein contain bacterial marker genes encoding resistance to antibiotics (e.g. Ampicillin) and other vector sequences. Therefore, genetically modified moulds will usually contain antibiotic resistance genes and other vector DNA.

Whereas, targeted integrations of a single gene copy have been described regularly (e.g. Timberlake, "Gene Cloning and Analysis" (Chapter 3) in the book "More Gene Manipulations in Fungi" (1991) 51–85, edited by Bennett and Lasure; Gouka et al. Applied and Environmental Microbiology 62 (1996) 1951–1957) it has been proven to be very difficult to obtain mould strains that contain multiple gene copies integrated at a predetermined locus in the genome. Gouka et al. (Curr. Genet. 27 (1995) 536–540) reported the selection of targeted multi-copy integrations at the pyrG locus in *A. awamori*, but the recombinant strains were obtained from transformations in which DNA was used containing vector sequences and no information was presented on the number of gene copies that were integrated at the pyrG locus. For *Aspergillus nidulans* a similar observation on targeted tandem integration at the argB locus was published (Van den Hondel and Punt, "Gene transfer systems and vector development" (Chapter 1) in the book "Applied Molecular Genetics" (1991) 1–28, edited by Peberdy et al.).

Several other publications indicate that site-directed integration of multiple gene copies could not be obtained, although it was desired for scientific or commercial purposes, (Kubicek-Pranz et al. J. of Biotech. 20 (1991) 83–94; Van den Hondel et al. Antonie van Leeuwenhoek 61 (1992) 153–160; Verdoes et al. Transgenic Research 2 (1993) 84–92; Archer et al. Antonie van Leeuwenhoek 65 (1994) 245–250; Van Gemeren et al. Applied Microbiology and Biotechnology 45 (1996) 755–763; Van Gemeren, "Expression and secretion of defined cutinase variants by *Aspergillus awamori*" (Chapter 5) Thesis University of Utrecht (1997) ISBN 90-393-1229-X).

4. Previously, two processes have been described in literature that, in principle, might allow the generation of mould strains that contain multiple copies of a gene that are integrated at a predetermined locus in the genome without the presence of other foreign DNA.

The first process describes the preparation of a protein by a fungus transformed by site-directed multicopy integration of an expression vector in the ribosomal DNA locus of the fungal genome as described in International PCT patent application WO-A-91/00920; Unilever, published Jan. 24, 1991. Although the Examples were carried out with yeasts, it was envisaged that such process is also applicable to moulds. Thus such process could make it possible to construct a mould strain in which multiple copies of a gene are integrated at a predetermined locus of the genome, without the presence of other foreign DNA.

However, transformation of moulds follows a somewhat different pattern than the transformation of yeasts. Whereas in the yeast *Saccharomyces cerevisiae* transforming DNA is integrated into the genome of the cell via homologous recombination at the corresponding homologous site, in filamentous fungi such as the mould *Aspergillus awamori* DNA integrates mainly via illegitimate recombination at random sites in the genome (Finkelstein, "Transformation" Chapter 6 in the book "Biotechnology of Filamentous Fungi" (1992) 113–156, edited by Finkelstein and Ball). For instance, for the mould *A. awamori* Gouka et al. (Curr. Genet. 17 (1995) 536–540) performed an analysis on a large number of transformants and showed that DNA integrated via homologous recombination in approximately 10% of the transformants, whereas the remaining 90% integrated randomly. This means that transformants have to be screened for site-directed integration events. Therefore, a process for transformation of moulds as described in WO-A-91/00920 would require lengthy screening procedures because DNA that is introduced into the mould cell can also integrate randomly and not only via homologous recombination at the predetermined site.

The second process describes the site-directed integration of a single gene copy whereby any other heterologous DNA used for cloning and any heterologous mould selection marker are removed, as described in European patent application EP-Al-0 635 574; Gist-brocades N.V., published Jan. 25, 1995.

If this second process would be used for preparing a transformed mould containing multiple gene copies, the process is very cumbersome, because the whole process need be repeated for each subsequent copy that needs to be introduced.

Although the repetition of the second process for obtaining multicopies is mentioned as simple statements in the specification (see e.g. page 3, lines 22–23, page 6, lines 21–25, page 7, lines 29–30, and page 8, lines 9–11, and 15–16), it was not shown in the Examples that it really works. In fact the statement "sequential application of the same technology" mentioned on page 8, lines 9–11 confirms the laborious character of this method for introducing multiple gene copies at predetermined loci, covering both a single site and multiple sites.

A further disadvantage of the method described is the risk that the earlier introduced desired foreign DNA is removed during a subsequent repetition of the process.

In summary, items 1–4 above show that there exists a need in the field of mould biotechnology to construct mould strains containing multiple copies of a gene encoding a desired protein that are integrated at a predetermined locus in the genome and that are free of bacterial antibiotic resistance genes or of other foreign DNA such as remnants of vector DNA used in cloning. Ideally, the recombinant microorganism should only contain the heterologous gene encoding the desired protein.

SUMMARY OF THE INVENTION

The invention is applicable in the field of mould biotechnology and provides a new and more advanced process for site-directed integration of multiple copies of a gene in a mould without leaving any undesired DNA, i.e. without leaving in the transformed mould the selection marker used for selection of transformants or other DNA used for cloning. The invention is based on the specific introduction of a double-strand break at the chromosomal target in the mould cell which significantly enhances site-directed integration at that locus. Repair of the break with a repair DNA homologous to the regions flanking the break and including multiple copies of at least one gene encoding at least one desired protein will lead to simultaneously integration of those multiple copies at the locus of the break.

The present invention provides a process for transforming a mould, in which (1) multiple copies of a desired gene are integrated in the chromosome of said mould, (2) the integration in the mould genome is site-directed via homologous recombination in contrast to the usual random integration of moulds, (3) such site-directed integration event is selected preferentially over any possible random integration event, e.g. by selecting for the restoration of a defective marker gene, (4) remaining foreign DNA sequences, e.g. antibiotic resistance genes and DNA originating from other organisms, can be avoided, and (5) a rare-cutting endonuclease, e.g. I-SceI, is used to introduce a double-strand break in the chromosomal DNA of the mould, Although the emphasis is given to the use of I-SceI as a rare-cutting endonuclease, it is envisaged that also other rare-cutting endonucleases can be used, including HO Endonuclease and VDE, the latter also being known as PI-SceI.

BRIEF DESCRIPTION OF THE DRAWINGS

FIG. 4. shows the construction of the plasmid pUR5729, in which

PexlA=Promoter sequences of the *A. awamori* 1,4-β-endoxylanase A gene, cut=coding region of the *F. solani pisi* cutinase gene (synthetic copy of CDNA), and TexlA=Terminator sequences of the *A. awamori* 1,4-β-endoxylanase A gene.

Figure 5:
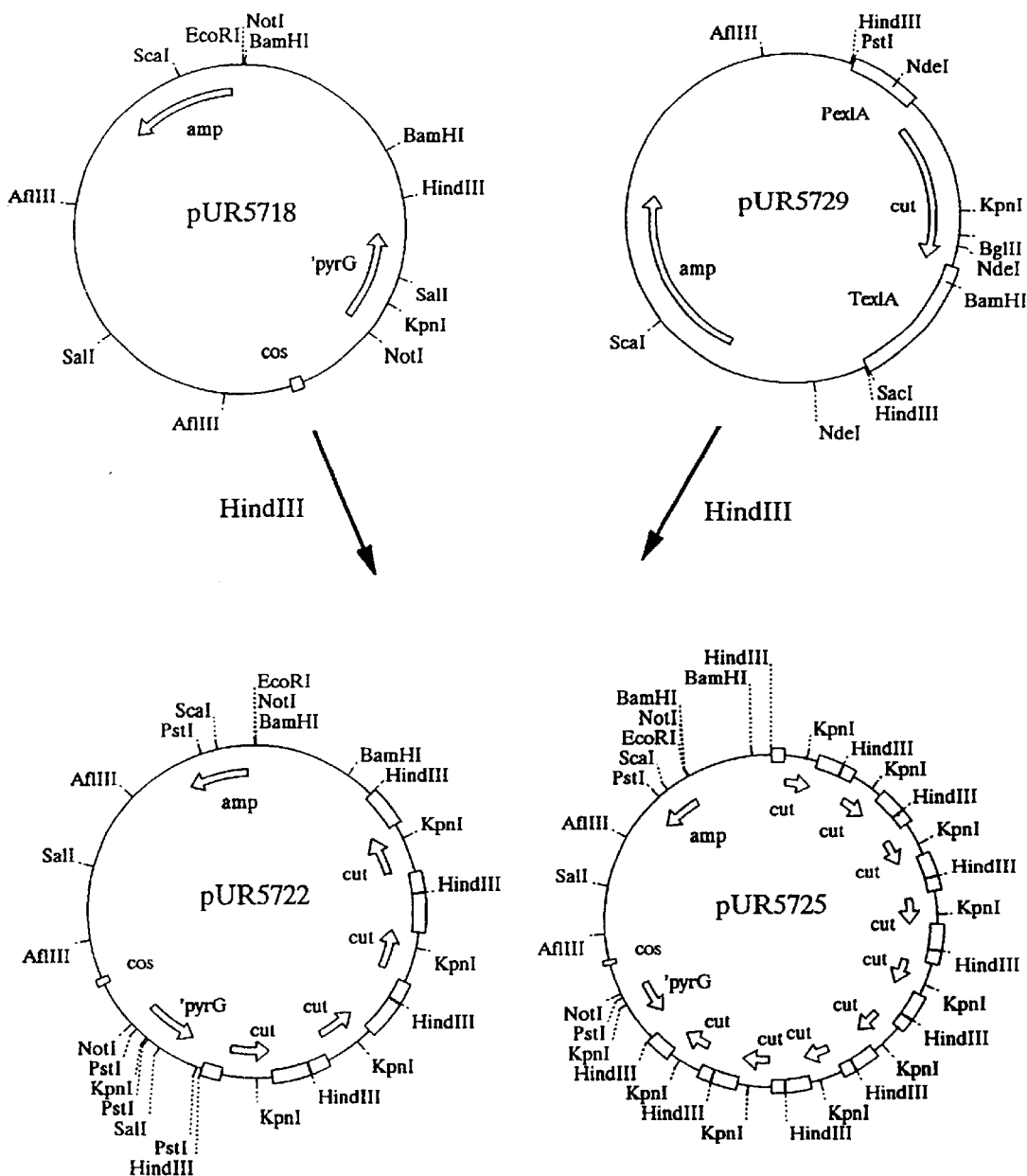

FIG. 5. shows the construction of the cosmids pUR5722 and pUR5725.

Figure 6:
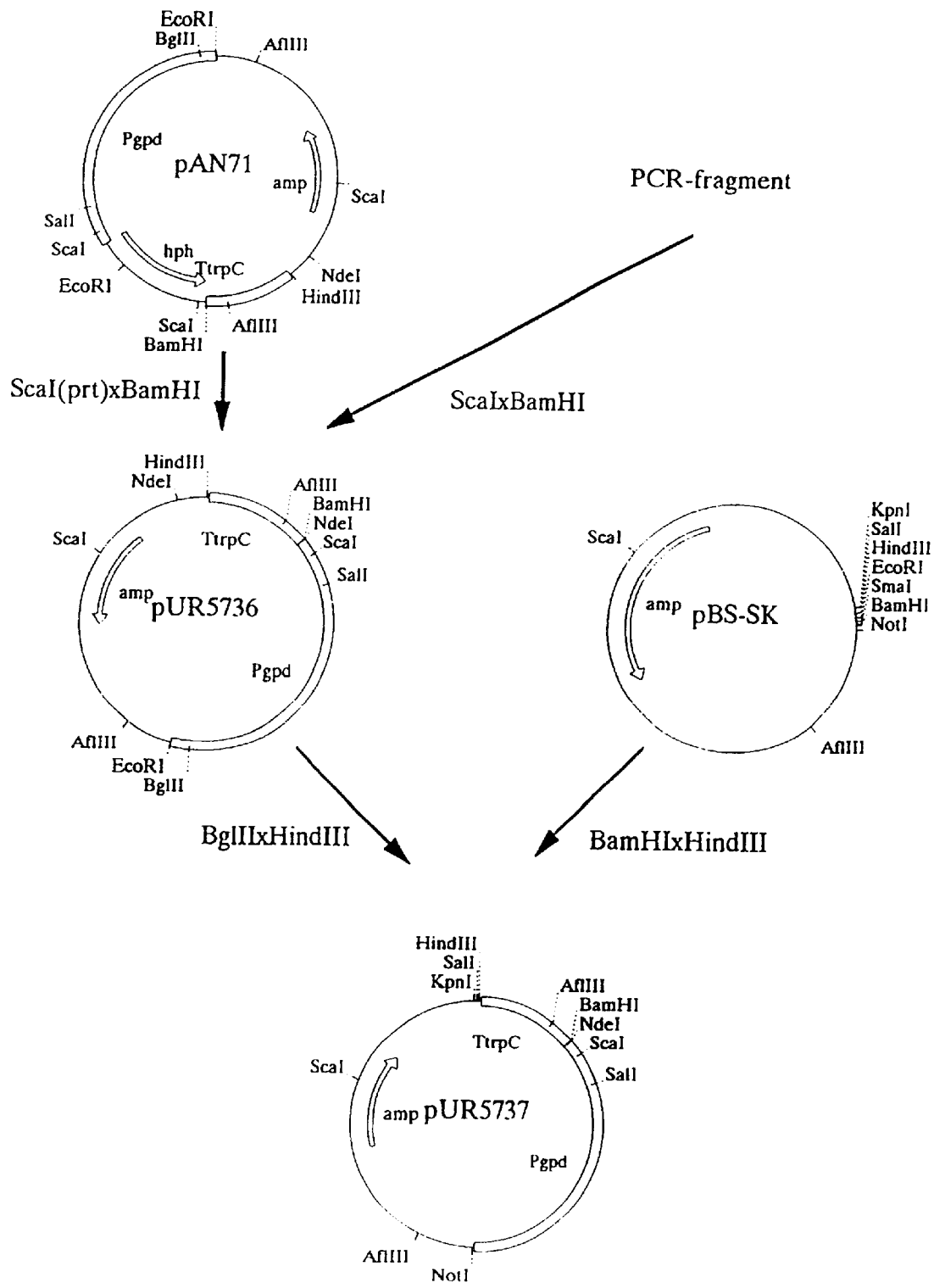

FIG. 6. shows the construction of the plasmids pUR5736 and pUR5737, in which

Pgpd=Promoter sequences of the *A. nidulans* gpd gene, hph=coding region of the hygromycin phosphotransferase gene from *E. coi*, and TtrpC=Terminator sequences from the *A. nidulans* trpc gene.

Figure 7:
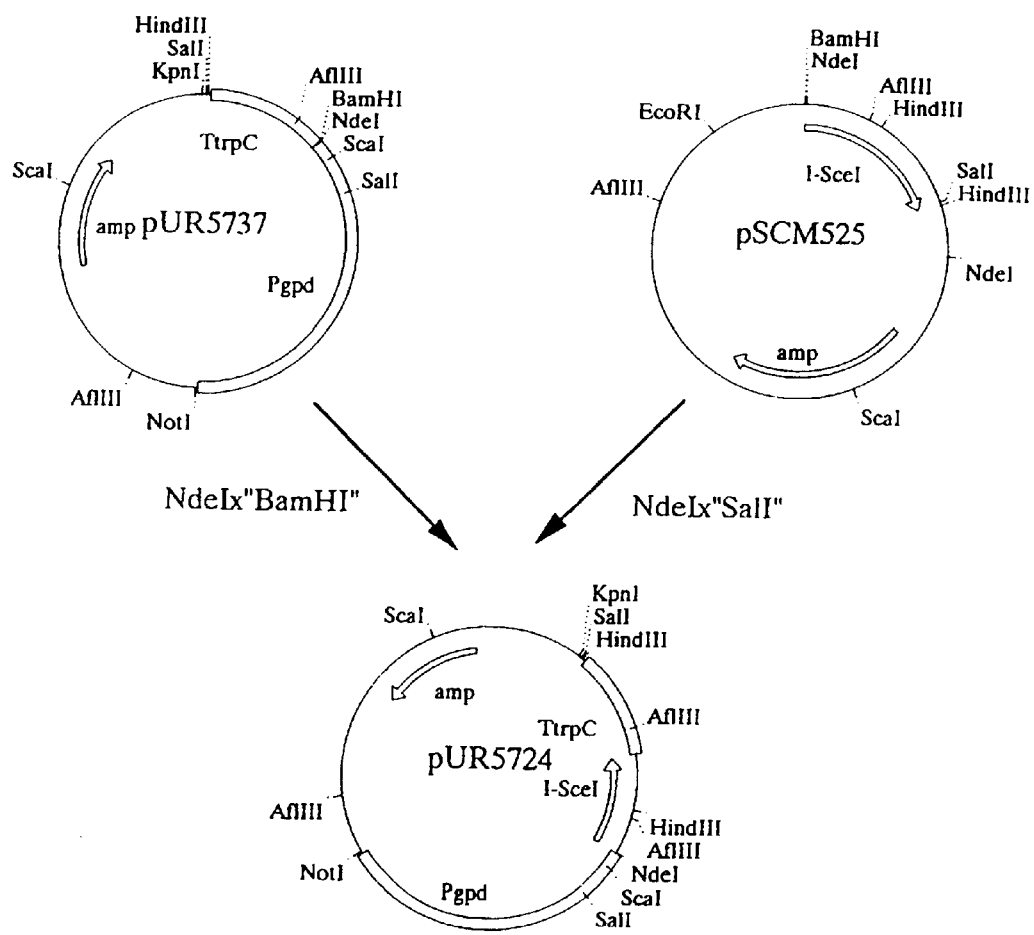

FIG. 7. shows the construction of plasmid pUR5724, in which

I-SceI=synthetic gene encoding the *Saccharomyces cerevisiae* I-SceI endonuclease.

Figure 8:
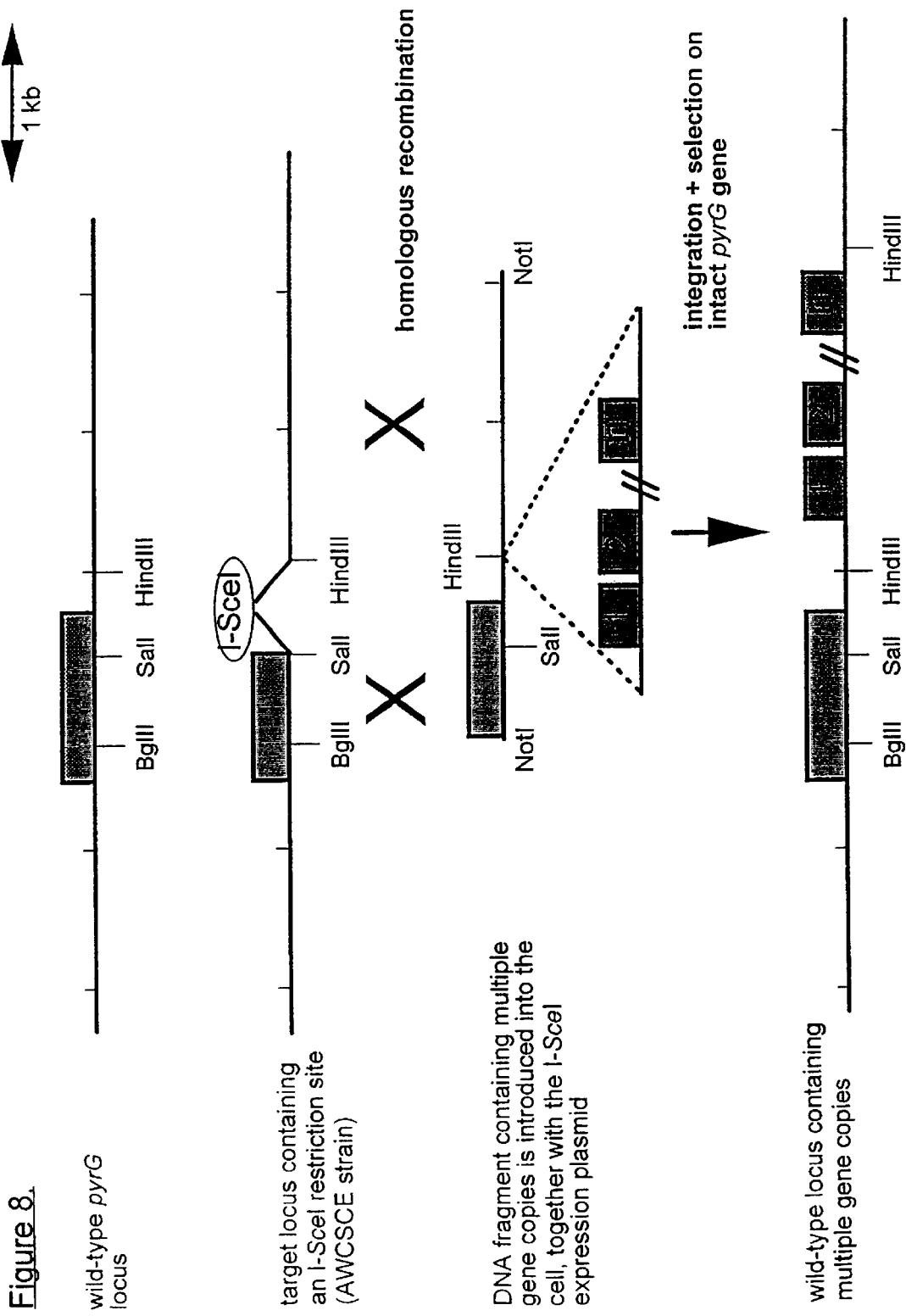

FIG. 8. Experimental design of the process for site-directed integration of multiple copies of a gene in the mould *A. awamori* using the I-SceI endonuclease. The wild-type pyrG gene is depicted in the upper part of the figure. The coding region of the gene is indicated by the light grey shaded box. Below this, the target locus containing the I-SceI restriction site as present in the *A. awamori* strain AWCSCE is shown. Between the non-functional 5' part of the pyrG gene and 3' flanking sequences of the chromosomal pyrG locus an I-SceI site is present. The fragment that is introduced into the strain AWCSCE contains a non-functional 3' part of the pyrG gene that is partially homologous to the mutated pyrG gene at the chromosomal target locus, one or multiple gene copies (indicated by the dark grey shaded boxes 1,2 and n) comprising at least one structural gene encoding at least one desired protein and an additional sequence from the pyrG locus that is homologous to sequences present immediately downstream of the I-SceI site at the target locus. Simultaneously, the I-SceI endonuclease or an expression plasmid containing the I-Scel gene is co-introduced into the cell. After homologous recombination induced by a double-strand break at the I-SceI site an intact pyrG gene is restored and the multiple gene copies are simultaneously integrated at the pyrG locus, which is illustrated in the lower part of the figure.

Figure 9:
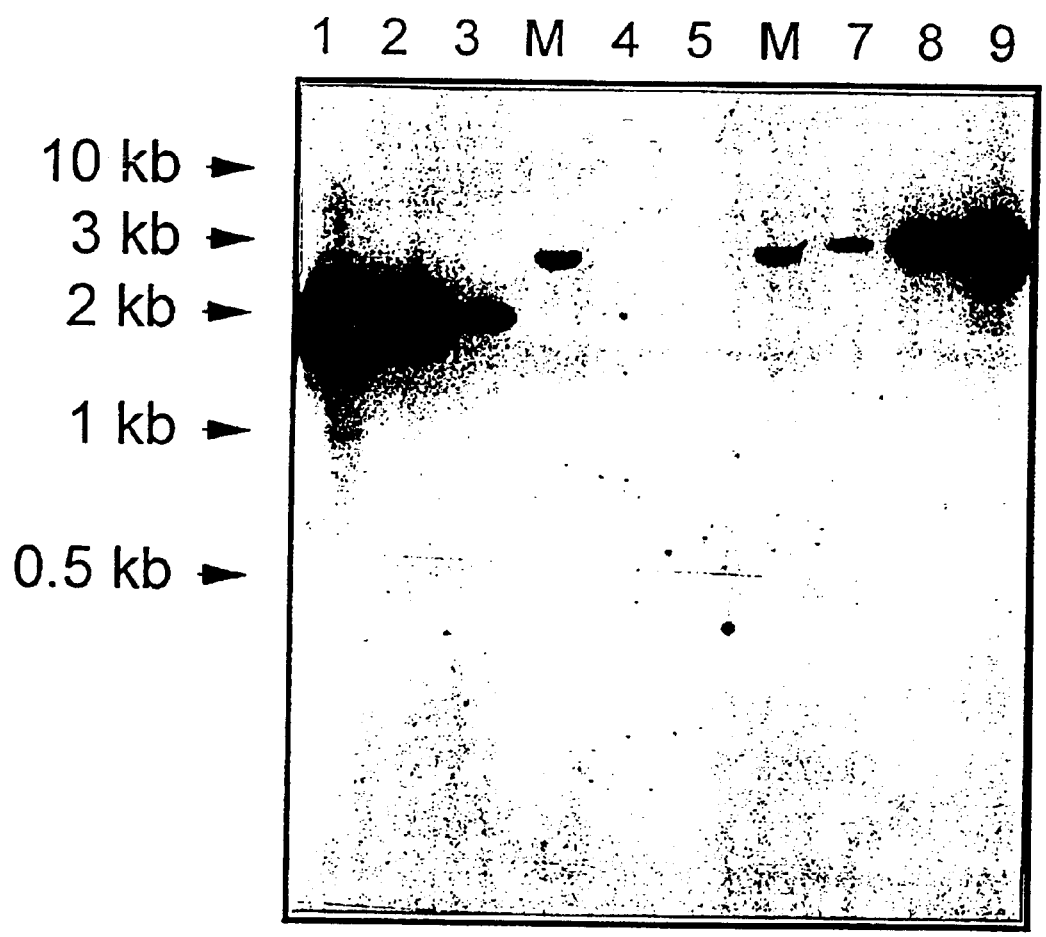

FIG. 9. shows the autoradiograph of the Southern blot of *A. awamori* genomic DNA probed with an 18 bp end-labelled oligonucleotide representing the I-SceI restriction site. The genomic DNA was digested with Sau3A. M represents the 1 kb DNA marker (BRL), lanes 1, 2 and 3 contain samples of the plasmid pSCM522 digested with HinfI (control DNA substrate containing the I-SceI restriction site, supplied with the I-SceI endonuclease from Boehringer Mannheim, cat. no. 1497235) in concentrations that correspond to 200, 20 and a single copy of the I-SceI restriction site(s) in the genome of *A. awamori*, respectively. Lanes 4 and 5 contain Sau3A digested genomic *A. awamori* DNA (7.5 μg). Lanes 6, 7 and 8 contain samples of plasmid pUR5712 in concentrations that correspond to a single copy, 20 and 200 copies of the I-SceI restriction site(s) in the genome of *A. awamori*.

Figure 10:
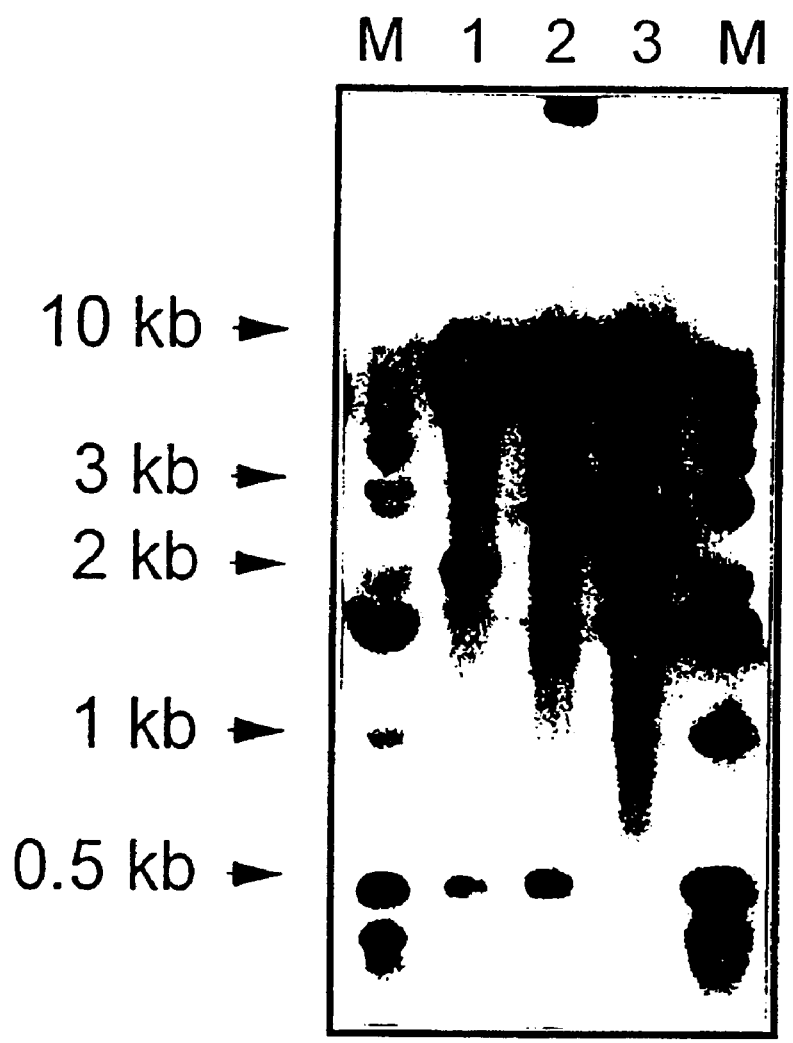

FIG. 10. shows the autoradiograph of the Southern blot of the two *A. awamori* mutant pyrG strains. The genomic DNA was digested with BglII and I-SceI and probed with a 2.4 kb BamHI×HindIII fragment from plasmid pAW4.1 containing the *A. awamori* pyrG gene. M represents the 1 kb DNA marker (BRL), Lane 1 and 2 contain genomic DNA of the *A. awamori* mutant pyrG strains. Lane 3 contains genomic DNA from the non-transformed wild-type *A. awamori* strain.

Figure 11:
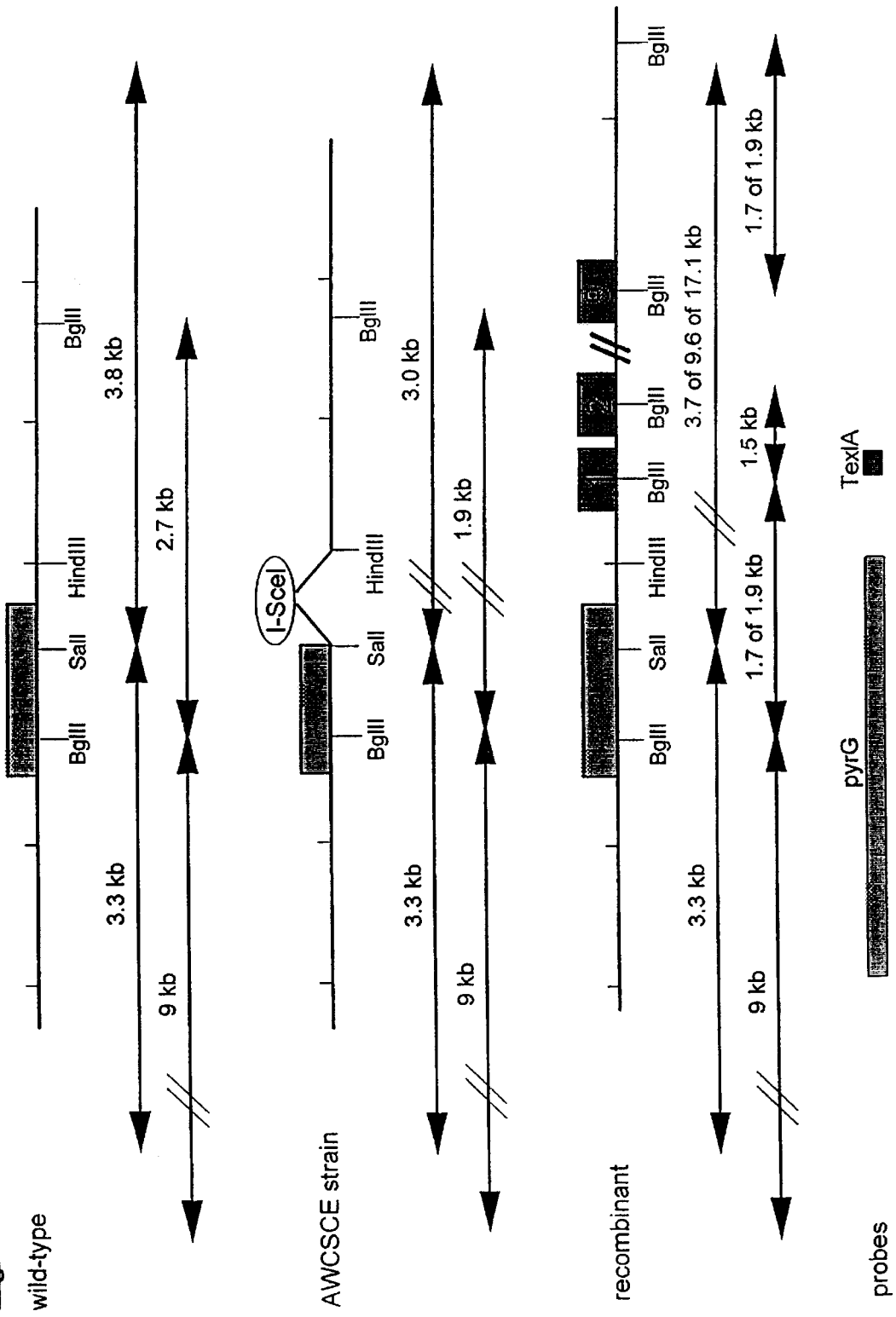
Figure 12:
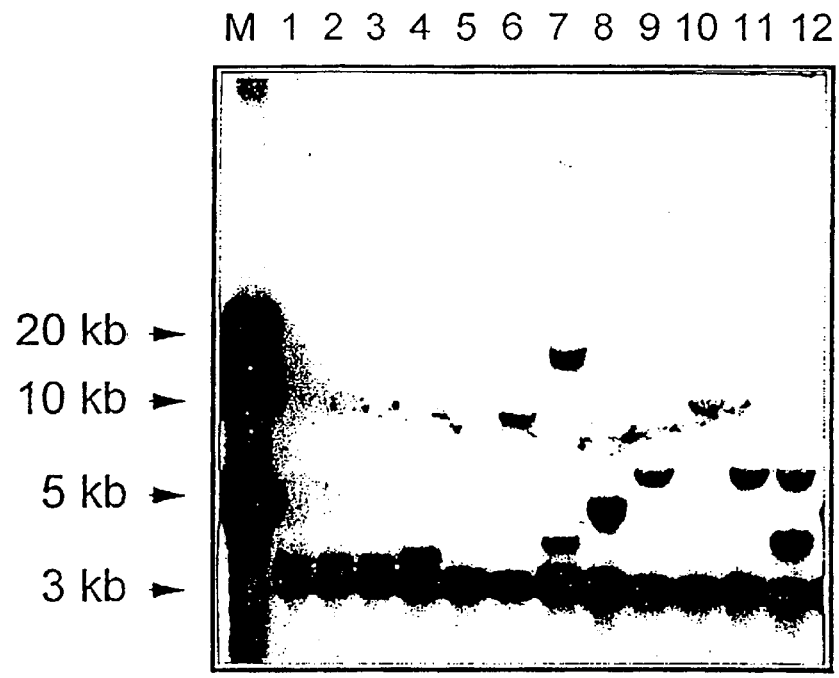
Figure 12:
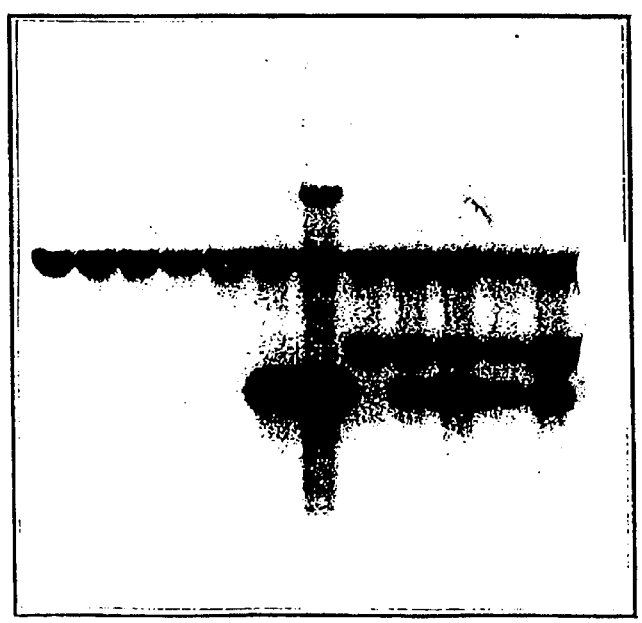

FIG. 11. Southern analysis of the recombinant strains obtained in the transformation of *A. awamori* strain AWC-SCE (see Example 4). The genomic DNA was digested with SalI or BglII and probed with a number of different probes (see Example 5). The two probes that are used in the Southern blots shown in FIG. 12 are indicated;

pyrG=a 2.4 kb BamHI×HindIII fragment from pAW4.1 containing the *A. awamori* pyrG gene.

TexlA=0.5 kb AflII×SacI fragment from pUR5729 containing the exlA terminator.

The wild-type pyrG gene is depicted in the upper part of the figure. The SalI digestion will give a 3.3 kb and a 3.8 kb fragment which fragments will hybridize with the pyrG probe. The BglII digestion will give a 9.0 kb and a 2.7 kb fragment, which fragments do not hybridize with the TexlA probe.

Below this, the target locus containing the I-SceI restriction site as present in the *A. awamori* strain AWCSCE is shown. The SalI digestion will give a 3.3 kb and a 3.0 kb fragment of which only the 3.3 kb fragment will hybridize with the pyrG probe. The BglII digestion will give a 9.0 kb and a 2.7 kb fragment, which fragments do not hybridize with the TexlA probe.

The lower part of the figure shows a restored pyrG gene containing none or multiple gene copies of the cutinase gene. The SalI digestion will give a 3.3 fragment and in recombinants obtained with pUR5718 a 3.7 kb fragment, in recombinants obtained with pUR5722 a 9.6 kb fragment and in recombinants obtained with pUR5725 a 17.1 kb fragment. All these fragments will hybridize with the pyrG probe. The BglII digestion will give a 9.0 kb fragment and in recombinants obtained with pUR5718 a 2.6 kb fragment, in recombinants obtained with pUR5722 or pUR5725 a 1.7 kb or a 1.9 kb fragment (depends on the orientation of the cutinase gene compared to the pyrG gene) and a 1.5 kb fragment, which is derived from the tandem repeat of the cutinase gene. Only the fragments containing the exlA terminator present in the cutinase expression cassette will hybridize with the TexlA probe.

The bottom part of the figure show the position of the pyrG and TexlA probes.

FIG. 12 (Parts A-B). shows the autoradiograph of the Southern blot analysis of the recombination events. M represents the 1 kb DNA marker (BRL), Lane 1: recombinant AWC-pUR5718#S1;
Lane 2: recombinant AWC-pUR5718#S2;
Lane 3: recombinant AWC-pUR5718#1;
Lane 4: non-transformed wild-type *A. awamori* strain;
Lane 5: *A. awamori* mutant pyrG strain AWCSCE;
Lane 6: recombinant AWC-pUR5725#1;
Lane 7: recombinant AWC-pUR5725#2;
Lane 8: recombinant AWC-pUR5722#A1;
Lane 9: recombinant AWC-pUR5722#A2;
Lane 10: recombinant AWC-pUR5722#B1;
Lane 11: recombinant AWC-pUR5722#B2;
Lane 12: recombinant AWC-pUR5722#B3.

A. The genomic DNA is digested with SalI and probed with the pyrG probe (see FIG. 11).

B. The genomic DNA is digested with BglII and probed with the TexlA probe.

DETAILED DESCRIPTION OF THE INVENTION

The invention provides a process for site-directed integration of multiple copies of a gene in a mould, which comprises (i) providing a mould cell containing in its chromosomal DNA a restriction site for a rare-cutting endonuclease, (ii) transforming such mould cell with a piece of DNA comprising in the 5' to 3' direction in the following order (a) a first DNA fragment homologous to part of the DNA upstream and in the neighbourhood of the restriction site for the rare-cutting endonuclease present in the chromosomal DNA of the mould (b) multiple copies of at least one expressible gene comprising a structural gene encoding a desired protein, (c) a second DNA fragment homologous to part of the DNA downstream and in the neighbourhood of the restriction site for the rare-cutting endonuclease present in the chromosomal DNA of the mould, while during the transformation of the mould the presence of the rare-cutting endonuclease is provided, (iii) selecting or screening for a mould cell in which the multiple gene copies of said expressible gene are inserted into the chromosomal DNA of the mould.

For site-directed integration it is desirable to use a restriction endonuclease forming a double-strand break at the target site, that does not form breaks at other loci in the chromosome, thus a rare-cutting endonuclease, an example of which is the I-SceI endonuclease from *Saccharomyces cerevisiae*. The nucleotide sequence encoding this enzyme and some uses of that sequence are described in International PCT patent application WO 96/14408; Institut Pasteur, published May 17, 1996. But also other known rare-cutting endonucleases can be used in a process according to the invention, e.g. VDE also known as PI-SceI (see M. Jasin; Trends In Genetics (TIG) 12 (No. 6, June 1996) 224–228; Genetic manipulation of genomes with rare-cutting endonucleases and M. Brenneman et al.; Proc. Natl. Acad. Sci. USA 93 (1996) 3608–3612; Stimulation of intra-chromosomal homologous recombination in human cells by electroporation with site-specific endonucleases) and HO Endonuclease (see M. Chiurazzi; The Plant Cell 8 (November 1996) 2057–2066; Enhancement of Somatic Intrachromosomal Homologous Recombination in Arabidopsis by the HO Endonuclease). Moreover, if a specific mould genome is practically free from restriction sites for a more familiar restriction endonuclease, such endonuclease can be used as well and can be considered a rare-cutting endonuclease for that specific mould genome.

The structural gene encoding the desired protein which gene forms part of the expressible gene can be homologous or heterologous to the mould.

In some cases the restriction site for the rare-cutting endonuclease occurs naturally in the chromosal DNA of the mould. But if the mould does not contain a restriction site for such rare-cutting endonuclease, the restriction site for the rare-cutting endonuclease can be introduced at a desired locus.

The selection of the transformed mould can be carried out by using a selectable marker. Preferentially, such selectable marker is a characteristic of a naturally-occurring, wild-type mould strain, while the mould strain to be transformed is a mutant strain thereof, deficient in said selectable marker, e.g. the orotidine-5'-phosphate decarboxylase gene (pyrG gene) which is present in wild-type *Aspergillus awamori*. But also other loci containing auxotrophic markers including trpc, argB, and niaD genes can be used, whereas other possible selectable markers include genes producing an easily assayable product. Sometimes the DNA introduced into the mould can be used as the selectable marker. For example, when the introduced DNA is expressed, it can result in a product not produced in the non-transformed mould, but which is more or less easily assayable. Or the presence or absence of the DNA can be determined by applying PCR techniques.

Preferably, the desired locus is within a selectable marker gene or in the neighbourhood thereof. In order to complement any disrupted or (partially) deleted gene the piece of DNA used for transforming the mould cell can comprise a third DNA fragment that completes any disrupted or (partially) deleted selectable marker gene in the chromosomal DNA. This would allow direct selection of strains containing the desired targeted integration of multiple copies of the gene.

The part of the DNA up-stream of the restriction site for the rare-cutting endonuclease present in the chromosomal DNA of the mould, to which the first DNA fragment is homologous, can be part of a selectable marker gene. Alternatively, the part of the DNA down-stream of the restriction site for the rare-cutting endonuclease present in the chromosomal DNA of the mould, to which the second DNA fragment is homologous, is part of a selectable marker gene. Or both the up-stream and down-stream parts can be part of the same selectable marker gene.

If two or more restriction sites for the rare-cutting endonuclease are present, the number of integrated gene copies can be increased or several different genes can be introduced at different loci, or both.

Preferably, the expressible gene comprises (1) a promoter operable in said mould, (2) optionally a DNA fragment encoding a secretion signal peptide facilitating the secretion of said desired protein from said mould, (3) a structural gene encoding said desired protein, and (4) optionally a terminator operable in said mould, whereby the promoter and the optional terminator control the expression of the structural gene. More preferably, the promoter, secretion signal and terminator are homologous to the mould to be transformed. In that case the amount of foreign DNA is kept to a minimum.

During the transformation of the mould the rare-cutting endonuclease can be provided by adding the endonuclease as such in way that is similar to Restriction Mediated Integration (REMI; Kuspa and Loomis, Proc. Natl. Acad. Sci. USA 89 (1992) 8803–8807; Redman and Rodriguez, Exp. Mycol. 18 (1994) 230–246). This is preferred when the amount of foreign DNA introduced into the mould should be as low as possible.

But for other reasons it can be convenient to form the rare-cutting endonuclease in situ by co-transforming the mould with DNA encoding the rare-cutting endonuclease, which DNA can be expressed during or after the transformation of the mould. Preferably, this DNA forms part of a plasmid that does not integrate in the genome, so that after further culturing the transformed mould strain can loose the plasmid while the desired DNA is still maintained in the genome. This event can be checked by further screening to confirm the absence of the rare-cutting endonuclease-encoding DNA in the genome of the recipient strain.

Preferably the mould belongs to the fungal division of Eumycota, more preferably to one of the fungal subdivisions Ascomycotina, Basidiomycotina, Deuteromycotina, Mastigomycotina, and Zygomycotina. It is especially preferred that the mould is selected from the genus Aspergillus, more particularly belonging to the species *Aspergillus awamori*. The invention also provides a transformed mould obtainable by a process according to the invention for the site-directed integration of multiple copies of a gene in a mould. Once a transformed mould according to the invention has been obtained, such transformed mould can be used in a process for further culturing.

The invention also provides a process for producing and optionally secreting a desired protein by culturing a transformed mould obtainable with a process as described above under conditions whereby the structural gene encoding said desired protein is expressed, and optionally isolating or concentrating the desired protein.

One way of introducing multiple copies of a gene is introducing several copies of the complete expression cassette as described below under the heading Construction of multi-copy vectors.

An alternative is by introducing several copies of the structural gene (polycistronic). After production of the encoded polypeptide it has to be cleaved to form the single peptides, e.g. by using the enzyme KEX 2.

The invention is exemplified by the following Example preceded by a description of the Materials and Methods that were used. In this Example the following is described.

EXAMPLE 1A

Experimental design of the process for site-directed integration of multiple copies of a gene in the mould *A. awamori* using the I-SceI endonuclease.

EXAMPLE 1B

Determination of the occurrence of a natural I-SceI restriction site in the genome of *A. awamori*.

EXAMPLE 1C

Construction of the *A. awamori* mutant pyrG strain AWC-SCE which contains an I-SceI restriction site at the locus of the mutated pyrG gene.

EXAMPLE 1D

Induction of site-directed integration at the pyrG locus by I-SceI expression.

EXAMPLE 1E

Southern blot analysis of recombination events.

MATERIALS AND METHODS

Bacterial and Mould Strains

For standard bacterial cloning the *Escherichia coli* strain DH5α (genotype: F, endA1, hsdR17 ($r_k^- m_k^+$), supE44, thi-1, lambda⁻, recA1, gyrA96, relA1, Δ (argF-lacIZYA)U169, deoR (phi80d(lacz)ΔM15); Hanahan; J. Mol. Biol. 166 (1983) 557–580) was used. For cloning multiple copies of a gene in a cosmid vector via packaging the *Escherichia coli* strain 1046 (Cami, B. and Kourilsky, P.; Nucleic Acids Research 5 (1978) 2381) was used.

The mould strain *Aspergillus awamori* #40 (a derivative of *A. awamori* CBS 115.52 also mentioned in WO 93/12237, page 9 line 13) was used to construct a pyrG derivative strain, designated AWCSCE, containing an I-Scel restriction site at the pyrG locus.

The preparation of *A. awamori* #40 (also known as *A. niger* var. *awamori* #40) was described in WO 91/19782 on page 13, lines 29–39, which read:

The production level of the *A.niger* var. *awamori* transformants, however, can be further increased by using suitable *A. niger* var. *awamori* mutant strains, such as *A.niger* var. *awamori* #40, which produces clearly more xylanase than the wild type strain. The mutant *A.niger* var. *awamori* #40 has been obtained by mutagenesis of *A. niger* var. *awamori* spores and selection for xylanase production. In bran medium the "xy1A" *A. niger* var. *awamori* #40 transformant produced 190 000 U xylanase, which is a considerable increase over the best producing *A.niger* var. *awamori* transformant.

In this specification the following endonuclease restriction sites are used:

| giving staggered ends | | giving blunt ends | |
|---|---|---|---|
| AflII | C↓TTAAG | SmaI | CCC↓GGG |
| BamHI | G↓GATCC | | |
| BglII | A↓GATCT | | |

-continued

| giving staggered ends | | giving blunt ends |
|---|---|---|
| EcoRI | G↓AATTC | |
| HindIII | A↓AGCTT | |
| HinfI | G↓ANTC | |
| NdeI | CA↓TATG | |
| NotI | GC↓GGCCGC | |
| PstI | CTGCA↓G | |
| SacI | GAGCT↓C | |
| SalI | G↓TCGAC | |
| Sau3AI | ↓GATC | |
| ScaI | AGT↓ACT | | and the rare-cutting restriction endonuclease from *Saccharomyces cerevisiae* I-SceI 18 bp:

5'-TAGATAACAGTAAT-3'    (see SEQ ID NO: 1)

Plasmid Constructions

Standard recombinant DNA techniques were used for cloning (Sambrook et al.; Molecular cloning—A laboratory manual. Cold Spring Harbor Laboratory, Cold Spring Harbor, N.Y. (1989)). In all cloning steps involving synthetic DNA linkers or PCR fragments, the correct DNA sequence of the linkers or PCR fragments was verified by DNA sequence analysis, using a Pharmacia LKB, ALF fluorescent sequencer.

Construction of the Target Site

Figure 1:
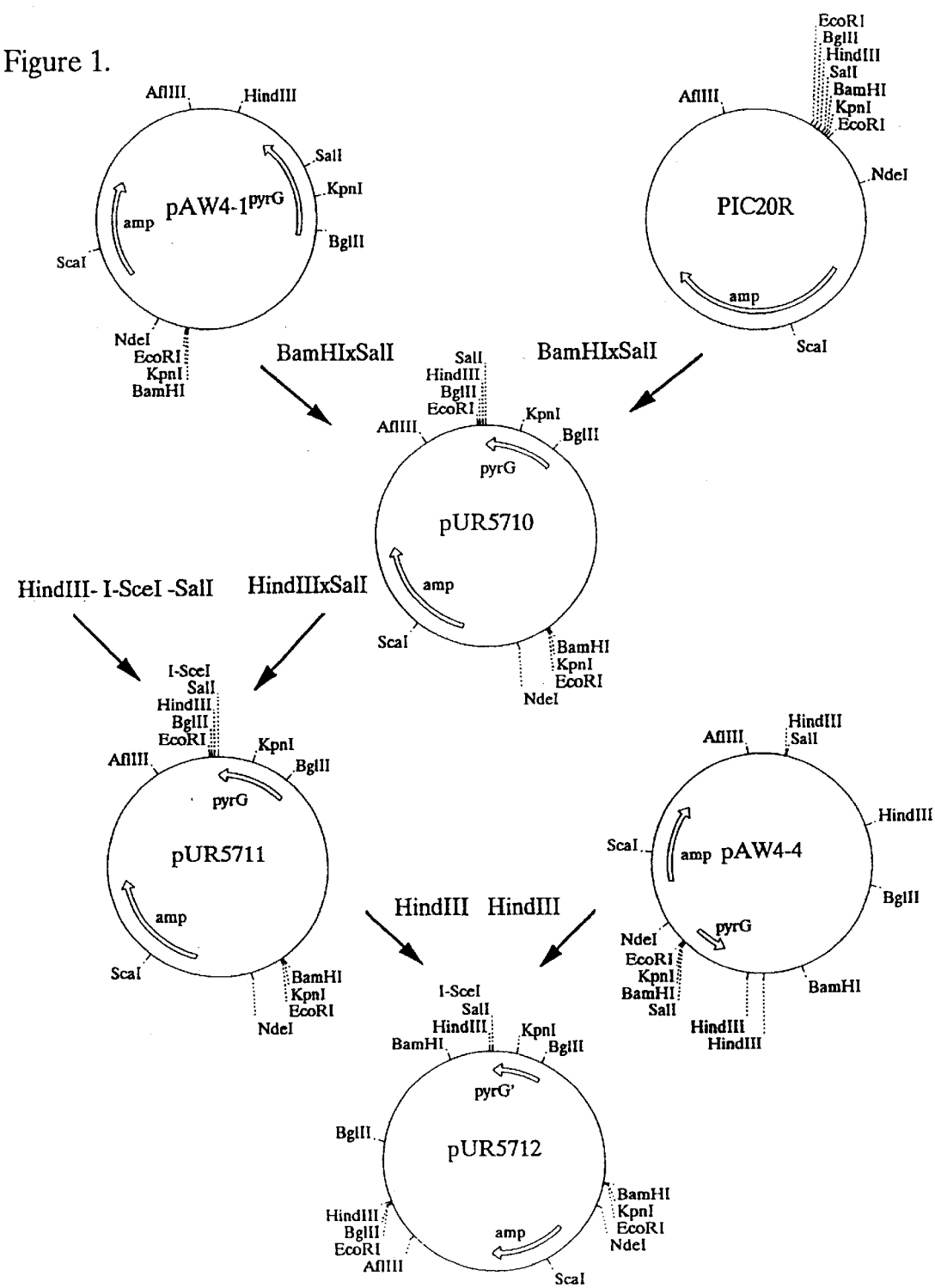
FIG. 1. shows the construction of the plasmids pUR5710, pUR5711 and pUR5712, in which amp=ampicillin resistance gene, and pyrG=pyrG gene from *A. awamori*, 'pyrG or pyrG' indicates that the gene is truncated at the 5' or 3' end, respectively.

The plasmid pUR5710 (see FIG. 1) was constructed by cloning a 2.0 kb BamHI/SalI fragment containing a 5' part of the pyrG gene, which is present on the plasmid pAW4.1 (Gouka et al.; Curr. Genet. 27 (1995) 536–540), into the general cloning vector pIC20R (Marsh et al.; Gene 32 (1984) 481–485) digested with BamHI and SalI. Subsequently, a synthetic DNA linker containing the 18 bp recognition site for the I-SceI endonuclease (5'-TAGATAACAGTAAT-3'; see SEQ ID NO: 1) flanked by SalI and HindIII sites was cloned into the plasmid pUR5710 digested with SalI and HindIII. This resulted in the plasmid pUR5711 (see FIG. 1). The plasmid pUR5712 (see FIG. 1) was constructed by cloning a 2.0 kb HindIII fragment containing sequences downstream of the pyrG coding region, which is present on the plasmid pAW4.4 (Gouka et al.; Curr. Genet. 27 (1995) 536–540), into the plasmid pUR5711 digested with HindIII. The orientation of this HindIII fragment compared to the coding region of the pyrG gene is identical to the wild-type situation. The plasmid pUR5712 was used to construct the *A. awamori* mutant pyrG strain AWCSCE.

Construction of the Repair Construct

Figure 2A:
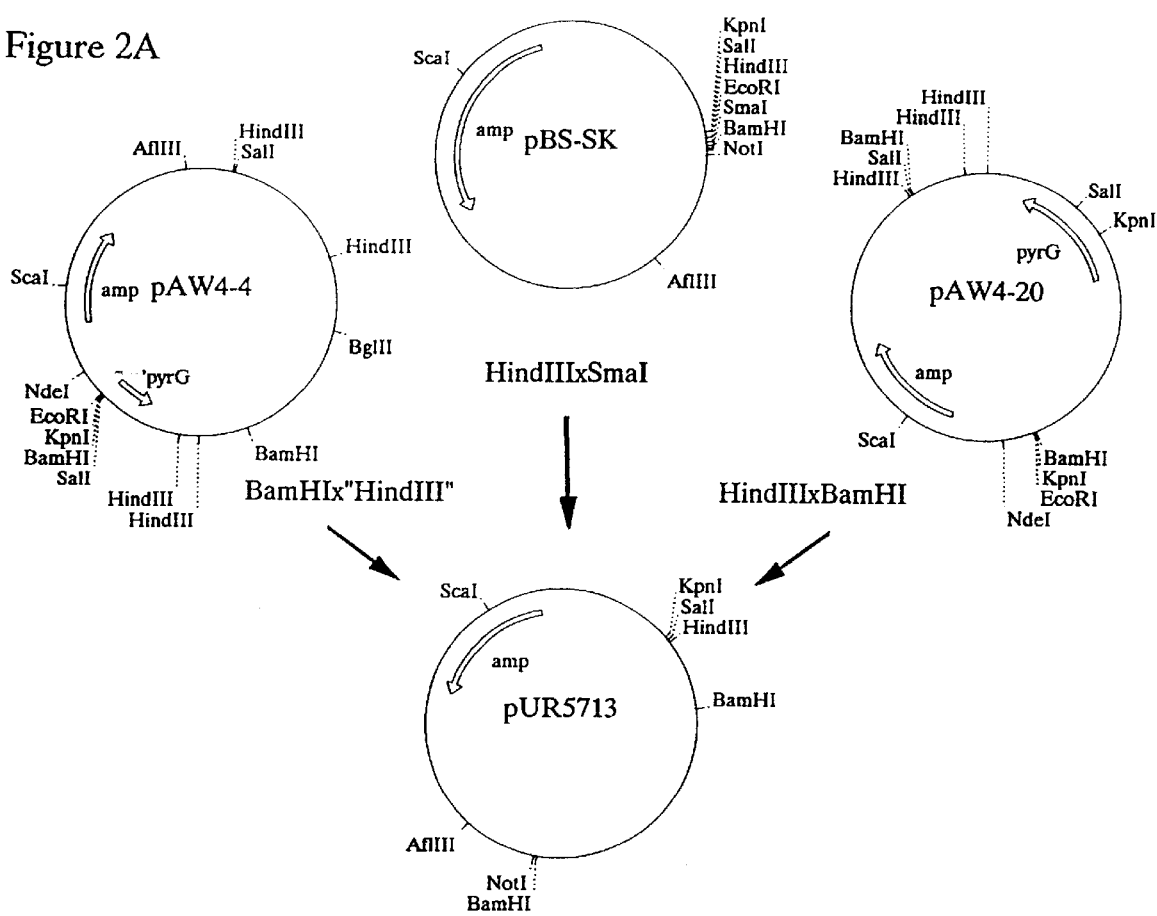
FIG. 2 (Parts A-B). shows the construction of the plasmids pUR5713 (FIG. 2A) and pUR5714 (FIG. 2B), in which pBS-SK=pBluescript$^R$-SK.
Figure 2B:
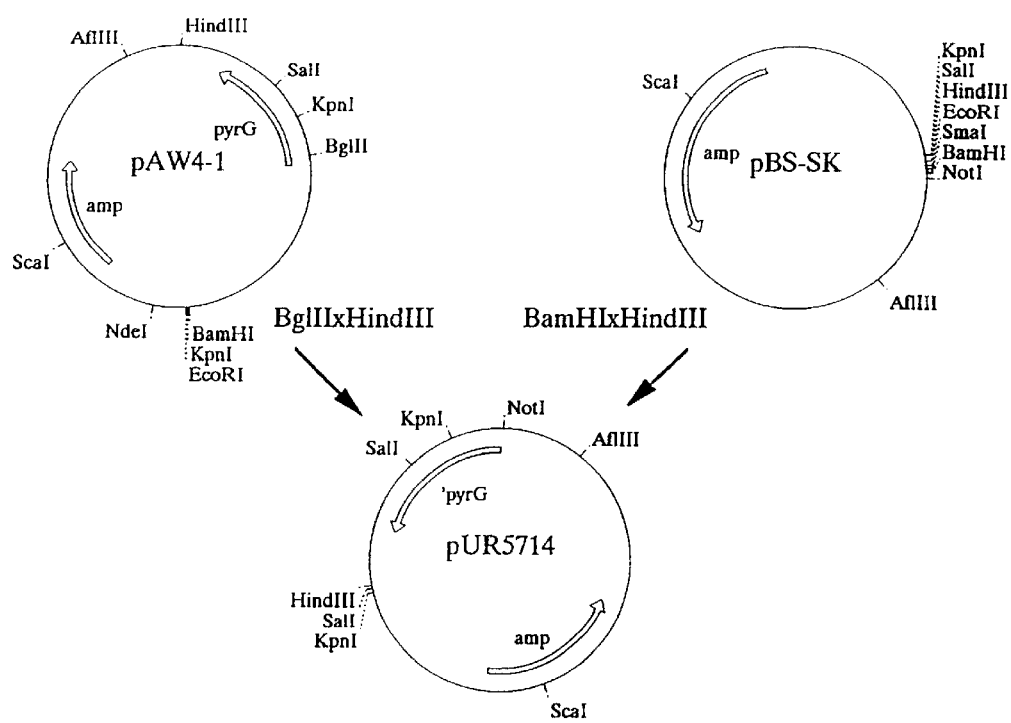
Figure 3:
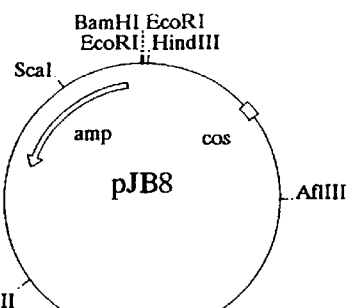
FIG. 3. shows the construction of the plasmids pUR5716 and pUR5718, in which cos=cos site.
Figure 3:
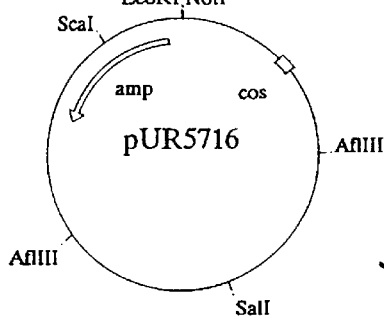
Figure 3:
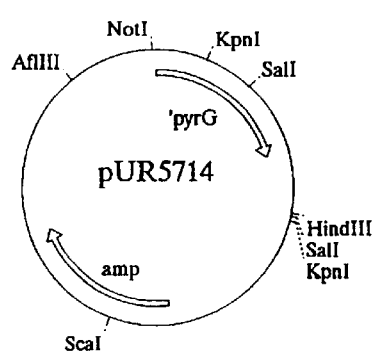
Figure 3:
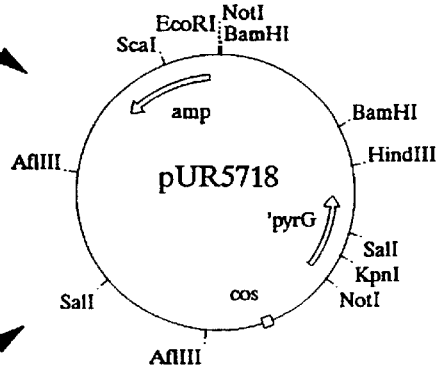
Figure 3:
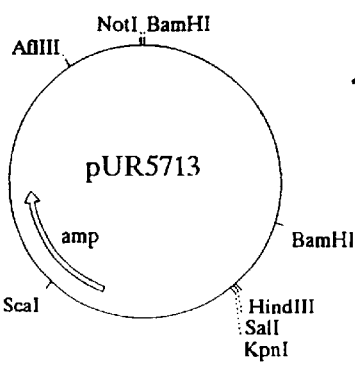

For the construction of the plasmid pUR5713 (see FIG. 2A) plasmid pAW4.4 was digested with HindIII, the HindIII site was filled in with Klenow and the fragment was subsequently digested with BamHI. The resulting 1.6 kb fragment, containing sequences down-stream of the pyrG coding region, was isolated. Furthermore, the plasmid pAW4.20 (Gouka et al.; Curr. Genet. 27 (1995) 536–540) was digested with BamHI and HindIII and the 0.4 kb fragment, containing sequences present immediately upstream of the 1.6 kb fragment described above, was isolated. The 0.4 kb HindIII/BamHI and 1.6 kb BamHI/filled in HindIII fragments were simultaneously cloned into the general cloning vector pBluescripT$^R$ SK (Stratagene) digested with HindIII and SmaI. This resulted in the plasmid pUR5713. The plasmid pUR5714 (see FIG. 2B) was constructed by cloning a 1.0 kb BglII/HindIII fragment containing a 3' part of the pyrG gene, which is present on the vector pAW4.1, into the general cloning vector pBluescript$^R$ SK digested with BamHI and HindIII. The cosmid pUR5716 (see FIG. 3) is derived from the cosmid vector pJB8 (Ish-Horowicz, D. and Burke, J. F.; Nucleic Acids Res. 9 (1981) 2989) by replacing the EcoRI/HindIII polylinker fragment by a synthetic linker containing an EcoRI and a NotI restriction site having the following sequence:

(5'-AATTC AT GCGCCGC T-3'

3'-G TA CGCCGCG ATCGA-5'        see SEQ ID NO: 2).

In this cloning step, the HindIII site is lost. The cosmid pUR5718 (see FIG. 3) was constructed by simultaneously cloning the 1.0 kb NotI/HindIII fragment from the plasmid pUR5714 and the 2.0 kb HindIII/NotI fragment from the plasmid pUR5713 into the plasmid pUR5716 digested with NotI. Thereby, this vector carries a sequence homologous to both sides of the I-SceI site at the pyrG target locus in the A. awamori mutant pyrG strain AWCSCE.

Construction of Multi-copy Vectors

Figure 4:
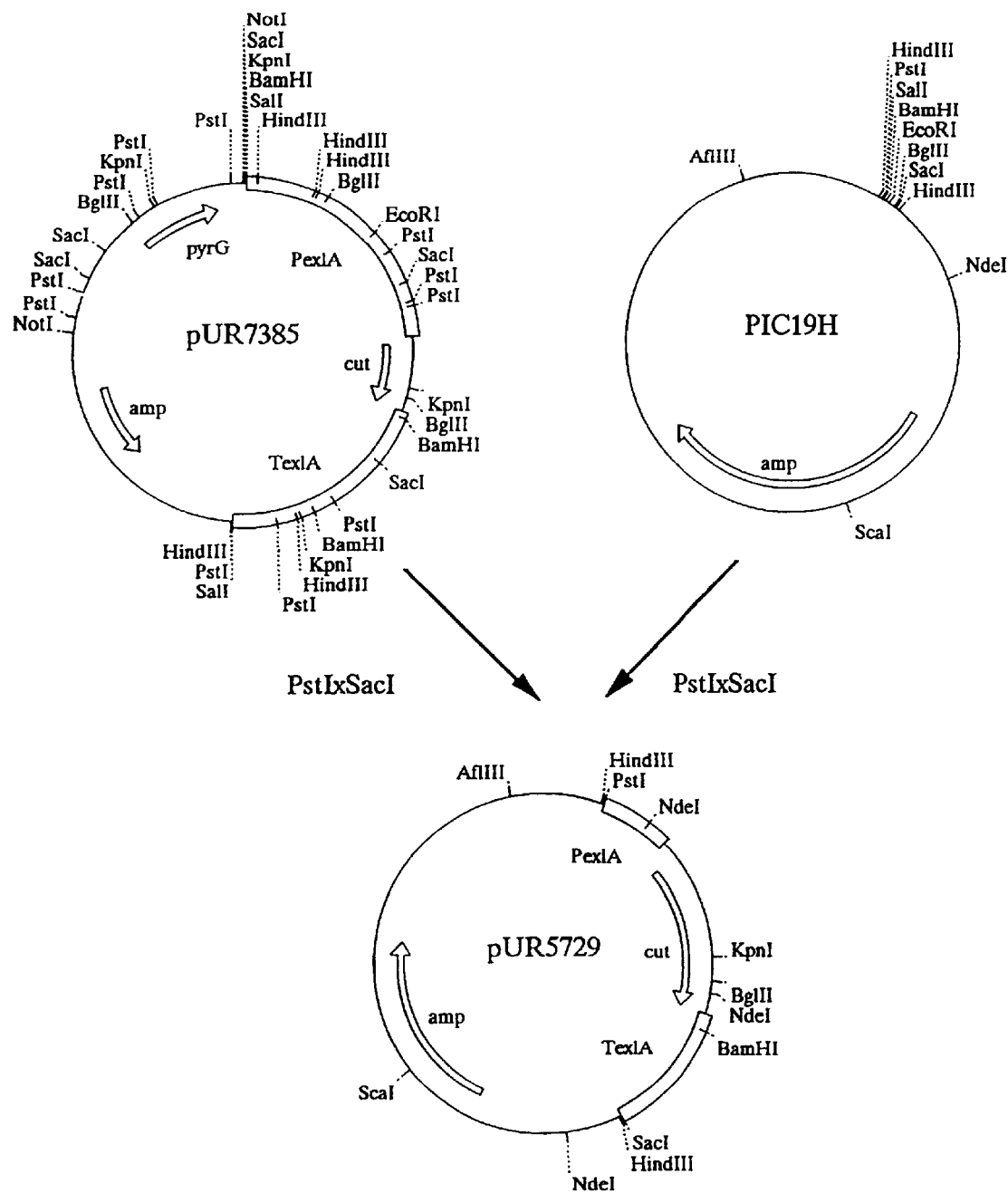

The plasmid pUR5729 (see FIG. 4) was constructed by cloning the 1.5 kb PstI/SacI fragment containing the open reading frame (ORF) of the cutinase gene from Fusarium solani pisi (synthetic copy of the cDNA; Van Gemeren et al.; Journal of Biotechnology 40 (1995) 155–162) under control of the promoter and terminator of the exlA gene from Aspergillus awamori (Gouka et al.; Applied Microbiology and Biotechnology 46, (1996) 28–35), from the plasmid pUR7385 (Van Gemeren et al.; Applied Microbiology and Biotechnology 45, (1996) 755–763), into the general cloning vector pIC19H (Marsh et al.; Gene 32 (1984) 481–485) digested with PstI and SacI. Based on the cosmid pUR5718 two new cosmids were constructed containing multiple copies of the cutinase gene under control of the exlA expression signals (as described above). A single copy of this expression cassette was isolated as a 1.5 kb HindIII fragment from the plasmid pUR5729 and ligated into the cosmid pUR5718 digested with HindIII. After transforming the ligation mixture into the E. coli strain DH5α, the cosmid pUR5722 (see FIG. 5) was obtained which contained a tandem array of four copies of the expression cassette. After packaging of the ligation mix using the λ-DNA in vitro packaging module (Amersham; code RPN1717), the packaging mix was transformed into E. coli strain 1046 (both according to the protocol provided with the module). From this transformation the cosmid pUR5725 (see FIG. 5) was obtained which contained a tandem array of nine copies of the expression cassette.

Construction of the I-SceI Expression Vector

The plasmid pUR5736 (see FIG. 6) was constructed by replacing a ScaI/BamHI fragment containing a part of the promoter from the A. nidulans gpd gene fused to the coding region of the E. coli hph gene, which is present on the plasmid pAN7.1 (Punt et al.; Gene 56 (1987) 117–124), by a PCR fragment containing the same promoter fragment fused to a NdeI and BamHI restriction site, digested with ScaI and BamHI. To obtain the vector fragment from the plasmid pAN7.1 the plasmid was only partially digested with ScaI, because the pUC backbone of the plasmid contains another ScaI site. The PCR fragment was obtained in a PCR reaction on the plasmid pAN7.1 using the primers MGpd1 (5'-GACAAGTCG-
    TTGCGTCAGTC-3';        see SEQ ID NO: 3)

and

MGpd2 (5'-CGATCCTT-
    CCATATGTGATGTCTGCTCAAGCG-3';  see SEQ ID NO: 4).

Subsequently, a BglII/HindIII fragment from the plasmid pUR5736 containing the promoter from the A. nidulans gpd gene and the terminator sequences from the A. nidulans trpC gene, was cloned into the BamHI/HindIII sites of the general cloning vector pBluescripT$^R$ SK. This resulted in the plasmid pUR5737. Hereafter, pUR5737 was digested with BamHI, this site was filled in using the Klenow enzyme, and a second digestion with NdeI was performed. The plasmid pSCM525 (kindly provided by Prof. Dr. B. Dujon, Institut Pasteur, Paris and described in U.S. Pat. No. 5,474,896; filed Nov. 5, 1992), containing a synthetic gene encoding the I-SceI endonuclease, was digested with SalI, this site was filled in using the Klenow enzyme, and a second digestion with NdeI was performed. The resulting fragment was cloned into the plasmid pUR5737 (NdeI/filled in BamHI fragment as described above) which resulted in the I-SceI expression vector pUR5724 (see FIG. 7).

Transformation Experiments

Preparation of Protoplasts

Conidia were obtained by growing the A. awamori strains at 30° C. on a nitrocellulose filter (Hybond-N, Amersham) placed on a PDA (Potato Dextrose Agar) plate for several days and subsequently washing the filters with physiological salt solution.

Protoplasts of A. awamori were prepared as described by Punt and Van den Hondel (Methods in Enzymology 216 (1993) 447–457). A shake flask containing 200 ml of MM medium (0.4 ml 1 M MgSO$_4$, 2 ml 100×spore elements (per liter; 60 g EDTA.2H$_2$O, 11 g CaCl$_2$.2H$_2$O, 7.5 g FeSO$_4$.7H$_2$O, 2.8 g MnSO$_4$.H$_2$O, 2.7 g ZnSO$_4$.7H$_2$O, 0.8 g CuSO$_4$.5H$_2$O, 0.9 g CoCl$_2$.6H$_2$O, 0.5 g Na$_2$MoO$_4$.2H$_2$O, 0.8 g H$_3$BO$_3$, 0.5 g KI, pH 4.0 with NaOH), 10 ml 20% glucose, 4 ml 50×AspA (3.5 M NaNO$_3$, 0.35 M KCl, 0.55 M KH$_2$PO$_4$, pH 6.5 with KOH)) including 0.5% yeast extract was inoculated with 10$^6$ conidia/ml of A. awamori and incubated for 18 hours at 30° C. in a shaker at 200 rpm. Mycelium was harvested through sterile Mirocloth$^R$ and washed with ice-cold 0.6 M MgSO$_4$. The mycelium was resuspended in OM medium (per liter: 500 ml 2.4 M MgSO$_4$, 480 ml H$_2$O, 16.8 ml 0.5 M Na$_2$HPO$_4$, 3.2 ml 0.5 M NaH$_2$PO$_4$, pH 5.8–5.9) at 5 ml/g mycelium. Subsequently, 5 mg Novozym 234$^R$ and 6 mg BSA were added per g mycelium. Protoplasting was allowed to proceed for 1–2 hours at 30° C. in a shaker at 80–100 rpm. The formation of protoplasts was checked using a light microscope. Protoplasts were filtered through sterile Miracloth$^R$ and the sample was divided in 30 ml aliquots in falcon tubes. STC (1.2 M sorbitol, 10 mM Tris/HCl pH 7.5, 50 mM CaCl$_2$.2H$_2$O) was added to bring the volume up to 50 ml and the protoplasts were harvested by centrifugation at 2000 rpm for 10 minutes at 4° C. The protoplasts were washed again in 50 ml STC and resuspended in STC at a concentration of approximately 10$^8$ protoplasts/ml.

PEG Transformations

Five to 7.5 µg of a single plasmid or two plasmids (in case the I-SceI expression plasmid is co-transformed) was added to an aliquot of 100 µl (10$^7$) protoplasts, mixed and incubated for 25 minutes on ice. PEG was added in two 200 µl aliquots and an 850 µl aliquot, and the mixture was incubated at room temperature for 20 minutes. Finally, the mixture was washed with 10 ml of STC, harvested by centrifugation at 2000 rpm for 10 minutes at room temperature and the sample was plated on a MM plate for selection of transformants.

Construction of the A. awamori mutant pyrG strain AWCSCE

Transformation of the wild-type A. awamori strain was performed with a purified (Qiaex gel extraction kit; Qiagen cat. no. 20021) EcoRI fragment obtained from the plasmid pUR5712 containing the mutant pyrG gene with the I-SceI restriction site at the site of the deletion (see FIGS. 1 and 8). Per transformation 2×10$^6$ protoplasts were transformed with 10 μg of DNA. Since pyrG strains are resistant to 5-FOA (5-fluoro-orotic acid; Boeke et al. Mol. Gen. Genet. 197 (1984) 345–346), pyrG transformants can be selected directly from wild-type strains. Transformants were selected on MM plates (AspA is replaced by AspA-N; 50×Aspa-N= 0.35 M KCl, 0.55 M KH$_2$PO$_4$, pH 6.5 with KOH) supplemented with 10 mM Uridine and 0.75 mg/ml of 5-FOA, with 10 mM proline as the N-source. The mutant phenotype of the transformants that were obtained was checked by growing these colonies on MM plates without uridine. Two transformants that were not able to grow without uridine were further analyzed by Southern blot analysis (FIG. 9 and see below).

DNA Isolation, PCR and Southern Analysis

Southern analysis was performed to confirm at a molecular level that the mould cell had been transformed and the desired DNA had been integrated into the genome. To obtain mycelium material for a genomic DNA isolation, approximately 10$^8$ mould conidia were inoculated in 50 ml of Aspergillus minimal medium supplemented with 0.5% yeast extract and incubated for a period ranging from 22 hours to 3 days at 30° C. in a shaker at 200 rpm. The mycelium was harvested through Miracloth$^R$ (Calbiochem) and snap frozen in liquid N$_2$. Frozen samples were ground to a fine powder using a Mikro-Dismembrator$^R$ (ex Braun Biotech International) for 1 minute at 1750 rpm. Mould genomic DNA was isolated using Qiagen genomic tips (cat. no. 10223) and a protocol for genomic DNA purification from filamentous fungi provided by the supplier. The step for digestion of cell wall material was omitted.

The PCR reactions were performed in a Perkin Elmer DNA Thermal Cycler 480 using approximately 1 μg genomic DNA, 25 pMol of each primer, 10 nMol of each dNTP, 1 unit of Taq DNA polymerase (Gibco-BRL) and 10 μl of 10×Taq DNA polymerase buffer in a total volume of 100 μl. The reactions were overlaid with mineral oil. The amplification was started with 5 min at 94° C. followed by 30 cycles of 1 min 94° C. 1 min 55° C. and 1 min 72° C. After the final cycle the elongation step was followed by another 5 min at 72° C. The sequence of the primers that were used are:

MGPyr1:
    5'-GCCAGTACACTACTTCTTCG-3'    (see SEQ ID NO: 5)

MGPyr2:
    5'-AGAGATCGCGAGAAGTTG-3'    (see SEQ ID NO: 6)

For the Southern blot, approximately 2.5 μg of DNA was digested with (a) restriction endonuclease(s) at 4 Units/μg for 16 hours. The following restriction endonucleases were used; Sau3AI, BglII, I-SceI and SalI. The DNA was separated on a 0.8% agarose TBE gel and transferred to a Hybond N membrane by capillary blotting (overnight). The membrane was (pre-)hybridized according to the Hybond protocol.

For the Southern blot presented in FIG. 9 the chromosomal DNA (7.5 μg) was digested with Sau3AI. The blot was probed with an 18 bp end-labelled oligonucleotide representing the I-SceI restriction site. This oligonucleotide was end-labelled using T4-polynucleotide kinase and γ-$^{32}$P-ATP. Hybridization was carried out for 4 hours at 42° C. The filter was washed for 5 minutes with 2×SSC at 42 ° C. followed by another 5 minutes with 2×SSC, 0.1% SDS at 42° C.

For the Southern blot presented in FIG. 10 the chromosomal DNA was digested with BglII or BglII and I-SceI. The 2.4 kb BamHI×HindIII pyrG fragment from pAW4.1 was used as a probe. A DNA probe labelled with α-$^{32}$P-dCTP was obtained using the RTS RadPrime DNA Labelling System from GibcosRL (cat. no. 10387-017). The electronic autoradiographs were obtained using an Instant Imager (Packard).

EXAMPLE 1A

Experimental Setup

The experimental design of the process for site-directed integration of multiple copies of a gene in the mould A. awamori using the I-SceI endonuclease is shown in FIG. 8. The system is based on three components, a fungal strain containing the target sequence with a I-SceI restriction site, a repair construct that is carrying sequences homologous to the target locus together with multiple copies of (a) gene(s) encoding (a) desired protein(s), and a plasmid containing an expression cassette with the gene encoding the I-SceI endonuclease. In order to specifically detect integration by homologous recombination we used the endogenous pyrG gene as a selectable marker gene (Gouka et al. Curr. Genet. 27 (1995) 536–540). First, we constructed a plasmid containing a defective pyrG gene in which a 0.8 kb region, encompassing the 3' end of the coding region and flanking terminator sequences, was replaced by the I-SceI restriction site (pUR5712). Using this plasmid the A. awamori mutant pyrG strain AWCSCE was constructed by a selection strategy for gene-replacement in fungi (see Materials and Methods). Second, the repair construct contains a complementary defective pyrG gene, in which 0.14 kb of the 5' end of the coding region is deleted, that has sequences homologous to both sides of the I-SceI site at the pyrG target locus in the A. awamori mutant pyrG strain AWCSCE. This repair construct contains an unique HindIII restriction site that can be used for inserting multiple copies of (a) gene(s) encoding (a) desired protein(s). The complete insert of the repair construct is flanked by NotI sites, which makes it possible to remove the vector sequences and transform A. awamori with only the insert fragment. Third, the expression cassette of the I-SceI gene consists of the promoter from the efficiently expressed glyceraldehyde-3-phosphate dehydroge-nase encoding gene from Aspergillus nidulans (gpdA) (Punt et al. Gene 56 (1987) 117–124), an artificial I-SceI ORF (U.S. Pat. No. 5,474,896; filed Nov.5, 1992) and the transcription termination region of the A. nidulans trpC gene (Mullaney et al. Mol. Gen. Genet. 199 (1985) 37–45). When the expression plasmid and the repair construct are co-introduced into protoplasts of the strain AWCSCE, transient expression of the I-SceI gene may lead to the introduction of double-strand breaks at the I-SceI site, thereby stimulating homologous recombination with the repair construct and integration of the multiple gene copies. Alternatively, the I-SceI endonuclease may be introduced directly into the cell in a way that is similar to Restriction Mediated Integration (REMI; Kuspa and Loomis, Proc. Natl. Acad. Sci. USA 89 (1992) 8803–8807; Redman and Rodriguez, Exp. Mycol. 18 (1994) 230–246; Brenneman et al. Proc. Natl. Acad. Sci. USA 93 (1996) 3608–3612). Because homologous recombination will restore an intact pyrG gene, these events can be selected directly by growing the transformed cells on MM plates without uridine.

EXAMPLE 1B

Determination of the Occurrence of a Natural I-SceI Restriction Site in the Genome of A. awamori Before the system of this invention was set-up, we determined whether naturally occurring I-SceI restriction sites are present in the genome of A. awamori. The I-SceI endonuclease has an 18 bp recognition site, which will statistically occur only once in $6.9 \times 10^{10}$ bp ($4^{18}$) or approximately once in every 18.500 *A. awamori* genomes. Therefore it seems unlikely that an I-SceI site will be present in the genome.

In order to determine the presence of a naturally occurring I-SceI site, a Southern blot was performed with *A. awamori* genomic DNA. The genomic DNA was digested with Sau3AI, which does not cut within the I-SceI restriction site, to create smaller fragments that are more suitable for Southern blotting and hybridization with a labelled oligonucleotide. Plasmid reconstructions with the plasmids pUR5712 and pSCM522 (control DNA substrate containing the I-SceI restriction site, supplied with the I-SceI endonuclease from Boehringer Mannheim, cat. no. 1497235), both containing a single I-SceI restriction site, representing a single copy site or 20 or 200 sites per genome were included as controls. The blot was probed with an 18 bp end-labelled oligonucleotide representing the I-SceI restriction site. For the autoradiograph see FIG. 9. Whereas the single copy reconstructions with the control plasmids show a clear hybridizing fragment (lanes 3 and 6), no hybridizing fragments are present in the lanes 4 and 5 containing the chromosomal *A. awamori* DNA. This result demonstrates that the genome of *A. awamori* does not contain a natural I-SceI restriction site. Thus, it is possible to specifically engineer an unique I-SceI site into the genome at a locus of choice and subsequently introduce an unique double-strand break in the genomic DNA at that locus by expressing the I-SceI gene in the cell or introducing the I-SceI endonuclease itself.

EXAMPLE 1C
Construction of the *A. awamori* Mutant pyrG Strain AWCSCE which Contains an I-SceI Restriction Site at the Locus of the Mutated pyrG Gene The *A. awamori* mutant pyrG strain AWCSCE is obtained by replacing the chromosomal wild-type pyrG gene with the mutant pyrG gene from pUR5712, which contains the I-SceI restriction site at the site of the deletion. Therefore, the *A. awamori* strain was transformed with a purified EcoRI fragment containing the insert from the plasmid pUR5712. Per transformation $2 \times 10^6$ protoplasts were transformed with 10 μg of DNA. In seven transformations a total of 11 5-FOA$^R$ colonies were obtained. All these transformants were not able to grow on MM plates without uridine, corresponding with a pyrG phenotype. Genomic DNA was isolated from these strains and a PCR was performed with the primers MGPyr1 and MGPyr2. These primers anneal within the regions flanking the deletion and will generate a 1.13 kb fragment when the wild-type pyrG gene is present and a 0.36 kb fragment when the mutant pyrG& gene is present. Two out of the 11 5-FOA$^R$ colonies contained the 0.36 kb fragment specific for the mutant pyrG gene and were further analyzed by Southern blotting. The remaining 9 5-FOA$^R$ colonies are likely to be the result of spontaneous mutations. DNA was digested with BglII and I-SceI and the blot was probed with a 2.4 kb BamHIxHindIII fragment from pAW4.1 containing the *A. awamori* pyrG gene (FIG. 10). In the DNA of both mutant strains and the wild-type strain a 9.0 kb BglII fragment was present. The other 2.7 kb BglII fragment, as present in the wild-type strain (lane 3), is absent in the mutant strains and replaced by a 0.5 kb BglIIxI-SceI fragment characteristic for the mutant pyrG gene carrying the I-SceI restriction site at the site of the deletion. This result indicates that these mutants originate from a replacement of the wild-type pyrG gene by the mutated pyrG gene from pUR5712. Because the mutant strain from lane 1 contains an additional unexplained hybridizing fragment of approximately 2.0 kb, the mutant strain from lane 2 was chosen for further experiments and designated AWCSCE.

EXAMPLE 1D
Induction of Site-directed Integration at the pyrG Locus by I-SceI Expression Protoplasts derived from the *A. awamori* mutant pyrG strain AWCSCE were transformed with a repair construct in the presence or absence of the I-SceI expression vector pUR5724. The repair constructs consisted of a mutant complementing pyrG gene (pUR5718), and derivatives thereof containing a repeat of 4 copies (pUR5722) or 9 copies (pUR5725) of a cutinase expression cassette. Prior to transformation, DNA from the repair constructs was digested with NotI. This released the insert from the vector sequences, thereby creating ends that are homologous to the target locus. The results of the transformation experiments are shown in table 1. The transformation frequencies were calculated from parallel transformations with the positive control construct pAW4.2, containing the wild-type pyrG gene.

Transformation of pUR5718 without the I-SceI expression vector pUR5724 yielded 16 recombinants corresponding to a gene targeting frequency of 10.6%, whereas including the I-SceI expression vector yielded 63 recombinants corresponding to a gene targeting frequency of 41.7%. These results indicate that gene targeting with the repair construct pUR5718 is stimulated approximately four-fold by the introduction of a double strand break at the pyrG locus in the strain AWCSCE.

Transformation of pUR5722, containing the repeat of 4 copies of the cutinase expression cassette, without the I-SceI expression vector pUR5724 yielded no recombinants. This means that the gene targeting frequency is lower than 3.6%. In contrast, transformation of pUR5722 with the I-SceI expression vector pUR5724 yielded 5 recombinants correspon-ding to a gene targeting frequency of 180%. These results indicate that gene targeting of a repair construct containing a tandem array of 4 copies of the cutinase gene is about 2 to 3 fold less efficient than that of the repair construct pUR5718 which only contains pyrG sequences. Moreover, these results indicate that gene targeting with the repair construct pUR5722 is stimulated at least five-fold by the introduction of a double strand break at the pyrG locus in the strain AWCSCE.

Transformation of pUR5725, containing the repeat of 9 copies of the cutinase expression cassette, without the I-SceI expression vector pUR5724 yielded also no recombinants. This means that in this case the gene targeting frequency is lower than 0.6%. In contrast, transformation of pUR5725 with the I-SceI expression vector pUR5724 yielded 2 recombinants corresponding to a gene targeting frequency of only 0.4%. These results indicate that gene targeting of a repair construct containing a tandem array of 9 copies of the cutinase gene is about 20 to 100 fold less efficient than that of the repair construct pUR5718 which only contains pyrG sequences.

In conclusion, these results demonstrated that gene targeting with the repair construct containing multiple gene copies of a heterologous gene was only possible when a double strand break was introduced at the pyrG locus in the strain AWCSCE. Gene targeting of a repair DNA becomes much more inefficient when an increasing number of gene copies are included with the repair construct. This further confirms the problem of site-directed integration of multiple gene copies as discussed in the section background of the invention and prior art.

EXAMPLE 1E
Southern Blot Analysis of Recombination Events

The wild-type pyrG phenotype of several recombinants was confirmed by streaking the conidia on MM plates. This was done for 9 and 10 recombinants obtained from transformations with pUR5718 in the absence or presence of the I-SceI, respectively, and all the recombinants obtained from transformations with pUR5722 and pUR5725. From ten of these transformants, conidia from individual colonies were streaked again on MM plates. Subsequently conidia were isolated and cultures were grown to obtain mycelium for genomic DNA isolation. DNA isolation and Southern analysis is described in Materials and Methods. The genomic DNA was digested with BlII or SalI. The Southern blots were probed with either the 2.4 kb BamHI×HindIII pyrG fragment from pAW4.1, the 0.46 kb AflII×SacI fragment encompassing the terminator region from the endoxylanase gene (pUR5729), the 0.72 kb BamHI×SalI fragment encompassing the I-SceI gene or the pJB8 vector. The experimental setup of the Southern analysis is shown in FIG. 11 and the autoradiographs of the Southern blots hybridized with the pyrG and TexlA probes are depicted in FIGS. 12A and B, respectively. In the Southern blot of wild-type A. awamori genomic DNA digested with SalI and probed with the 2.4 kb pyrG fragment a 3.3 kb and 3.8 kb fragment are present (FIG. 12A, lane 4). In the mutant strain AWCSCE the 3.8 kb fragment is replaced by a 3 kb fragment (FIG. 12A, lane 5). In recombinants obtained with the plasmid pUR5718 restoration of an intact pyrG gene will lead to a replacement of the 3 kb fragment with a 3.7 kb fragment (FIG. 12A, lane 1–3). The small difference in size of the latter fragment compared to the same fragment in the wild-type strain is caused by a small 0.15 kb marker deletion in the 3' flanking sequence of the pyrG gene in the repair construct pUR5718. Because there is no SalI site present within the cutinase expression cassette, site-directed integration of multiple cutinase gene copies in recombinants obtained with the plasmids pUR5722 (four cutinase gene copies) and pUR5725 (nine cutinase gene copies) is expected to lead to a replacement of the 3 kb fragment with a 9.6 kb or a 17.1 kb fragment, respectively. This replacement is observed for one pUR5725 recombinant (lane 7) and one pUR5722 recombinant (lane 10), which demonstrates the successful one step site-directed integration of multiple gene copies in A. awamori. Unexpectedly, in the other recombinants one or more copies of the cutinase gene have been lost during recombination. The remaining pUR5722 recombinants contain two copies of the cutinase gene (FIG. 12A, lane 9, 11 and 12) or only one copy (FIG. 12A, lane 8). The other pUR5725 recombinant (FIG. 12A, lane 6) contains three copies of the cutinase gene.

FIG. 12B depicts the Southern blot of genomic DNA digested with BglII and probed with the TexlA probe. This probe hybridizes with the endogenous exlA gene and the introduced multiple copies of the cutinase expression cassette. Thus the wild-type strain, the mutant AWCSCE strain and the recombinants obtained with pUR5718 contain only a 6 kb BglII fragment representing the endogenous exlA gene (lanes 1–5). Because the cutinase expression cassette contains one BglII site, this digestion will generate a 1.5 kb fragment in the recombinants containing multiple copies of the cutinase gene. The intensity of this repeat fragment relative to the endogenous exlA fragment is an indication for the number of cutinase gene copies that are present. The recombinants obtained with pUR5725 (lane 6 and 7) contain the additional 1.5 kb fragment. The intensities of the bands correspond well to the presence of three (lane 6) or nine copies (lane 7) of the cutinase gene as was also determined by the total size of the fragments (FIG. 12A). The same is true for the recombinants obtained with pUR5722. Due to the orientation of the cutinase gene copies relative to the pyrG gene (see FIG. 5) the BglII digestion will generate the 1.5 kb repeat fragment and a 2 kb border fragment. The recombinant in lane 8 contains only the repeat fragment, indicating the presence of one copy of the cutinase gene. The recombinants in lanes 9, 11 and 12 contain a repeat fragment that has the same intensity as the border fragment, which confirms the presence of two copies of the cutinase gene. The recombinant is lane 10 contains a repeat fragment that is about three times more intense than the border fragment which confirms the presence of four copies of the cutinase gene. In order to determine if other DNA, such as cosmid vector sequences, or the plasmid containing the I-SceI expression cassette had co-integrated into the genome in the recombinant lines, the Southern blots have also been probed with the 0.72 kb BamHI×SalI fragment encompassing the I-SceI gene (BglII digested DNA) or the pJB8 vector (SalI digested DNA). These blots demonstrated that in none of the recombinants, except for the pUR5725 recombinant containing nine copies of the cutinase gene, other DNA had been integrated (results not shown). This demonstrates that it is possible to construct "food-grade" strains that contain multiple copies of a gene without the presence of other foreign DNA. It should be noted that in the experiments described here the inserts of pUR5722 and pUR5725 had not been purified from the vector DNA prior to transformation, whereas this is possible. Moreover, it may be possible to omit the use of the I-SceI expression vector by transforming the endonuclease directly. These modifications will further improve the selection of strains that do not contain other foreign DNA.

This Example shows that advantages of this process for site-directed integration of multiple copies of a gene in a mould are:

- multiple gene copies can be introduced at a predetermined locus in the genome;
- the possibility to obtain site-directed integration of multiple gene copies in the genome is significantly improved by the introduction of a specific double-strand break at the chromosomal target in the mould cell; and
- the method results in a mould strain without residues of bacterial antibiotic resistance markers or other bacterial sequences like origins of replication, which the consequence that the resulting mould strains or products derived therefrom are so-called "food-grade" products.

REFERENCES

Archer et al. Antonie van Leeuwenhoek 65 (1994) 245–250
Boeke et al. Mol. Gen. Genet. 197 (1984) 345–346
Brenneman et al. Proc. Natl. Acad. Sci. USA 93 (1996) 3608–3612
Cami, B. and Kourilsky,P.; Nucl. Acids Res. 5 (1978) 2381
Choulika et al. Mol. Cell. Biol. 15 (1995) 1968–1973
Choulika et al. International Application published under the Patent Cooperation Treaty, WO 96/14408 (1996)
Colleaux et al. Cell 44 (1986) 521–533
Colleaux et al. Proc. Natl. Acad. Sci. USA 85 (1988) 6022–6026
Dujon et al., Institute Pasteur, Paris and described in U.S. Pat. No; 5,474,896; filed Nov. 5, 1992
De Massy and Nicolas, EMBO-J 12 (1993) 1459–1466
Gimble and Thorner, Nature 357 (1992) 301–306

Gouka et al. Applied and Environmental Microbiology 62 (1996) 1951–1957
Gouka et al.; Applied Microbiology and Biotechnology 46, (1996) 28–35
Gouka et al.; Curr. Genet. 27 (1995) 536–540
Halfter et al. Mol. Gen. Genet. 231 (1992) 186–193
Hanahan; J. Mol. Biol. 166 (1983) 557–580
Hamilton et al.; Proc. Natl. Acad. Sci. USA 93 (1996) 9975–9979
Ish-Horowicz, D. and Burke, J. F.; Nucleic Acids Res 9 (1981) 2989
Jasin, TIG 12 (1996) 224–228
Kucherlapati, R. and G. R. Smith (1988) editors, Genetic recombination, Washington DC: American Society of Microbiology
Kuspa and Loomis, Proc. Natl. Acad. Sci. USA 89 (1992) 8803–8807
Lee et al. Plant Cell 2 (1990) 415–425
Lin et al., Mol. Cell. Biol. 4 (1984) 1020–1034
Marsh et al.; Gene 32 (1984) 481–485
Meselson and Radding, Proc. Natl. Acad. Sci. USA 72 (1975) 358–361
Mullaney et al. Mol. Gen. Genet. 199 (1985) 37–45
Nicolas et al. Nature 338 (1989) 35–39
Offringa et al. EMBO-J 9 (1990) 3077–3084
Paszkowski et al. EMBO-J 7 (1988) 4021–4026
Puchta et al. Nucleic Acids Research 21 (1993) 5034–5040
Puchta et al. Proc. Natl. Acad. Sci. USA 93 (1996) 5055–5060
Punt et al.; Gene 56 (1987) 117–124
Punt and Van den Hondel; Methods in Enzymology 216 (1993) 447–457
Redman and Rodriguez, Exp. Mycol. 18 (1994) 230–246
Rouet et al. Proc. Natl. Acad. Sci. USA 91 (1994) 6064–6068
Rouet et al. Mol. Cell. Biol. 14 (1994) 8096–8106
Royer et al.; Bio/Technology 13 (1995) 1479–1483
Sambrook et al.; Molecular cloning—A laboratory manual. Cold Spring Harbor Laboratory, Cold Spring Harbor, N.Y. (1989)
Sargent et al. Mol. Cell. Biol. 17 (1997) 267–277
Smith et al. Nucleic Acids Research 24 (1995) 5012–5019
Strathern et al. Cell 31 (1982) 183–192
Sun et al. Nature 338 (1989) 87–90
Sun et al. Cell 64 (1991) 1155–1161
Szostak et al., Cell 33 breaks (1983) 25–35
Thomas and Cappechi, Nature 346 (1990) 847–850
Timberlake, "Gene Cloning and Analysis" (Chapter 3) in the book "More Gene Manipulations in Fungi" (1991) 51–85, edited by Bennett and Lasure
Van den Hondel et al.; "Heterologous gene expression in filamentous fungi" (Chapter 18) in the book "More Gene Manipulations in Fungi" (1991) 397–428, edited by Bennett and Lasure
Van den Hondel and Punt, "Gene transfer systems and vector development" (Chapter 1) in the book "Applied Molecular Genetics" (1991) 1–28, edited by Peberdy et al.
Van den Hondel et al. Antonie van Leeuwenhoek 61 (1992) 153–160
Van Gemeren et al.; Journal of Biotechnology 40 (1995) 155–162
Van Gemeren et al.; Applied Microbiology and Biotechnology 45, (1996) 755–763
Van Gemeren, "Expression and secretion of defined cutinase variants by *Aspergillus awamori*" (Chapter 5) Thesis University of Utrecht (1997) ISBN 90-393-1229-X
Verdoes et al. Transgenic Research 2 (1993) 84–92
Verdoes, "Strain improvement strategies for the overproduction of fungal proteins by filamentous fungi" (Chapter 1) Thesis Free University Amsterdam (1994)
Verdoes et al.; Appl. Microbiol. Biotechnol. 43 (1995) 195–205
Wenzlau et al. Cell 56 (1989) 421–430
Zimmer and Gruss, Nature 338 (1989) 150–153
Zin and Butow, Cell 40 (1985) 887–895

What is claimed is:

1. A process for the site-directed integration of multiple copies of a gene in a mould, which comprises
   (i) providing a mould cell containing in its chromosomal DNA a restriction site for a rare-cutting endonuclease,
   (ii) transforming such mould cell with a piece of DNA comprising in the 5' to 3' direction in the following order
       (a) a first DNA fragment homologous to part of the DNA upstream of the restriction site for the rare-cutting endonuclease present in the chromosomal DNA of the mould
       (b) multiple copies of at least one expressible gene comprising a structural gene encoding a desired protein,
       (c) a second DNA fragment homologous to part of the DNA downstream of the restriction site for the rare-cutting endonuclease present in the chromosomal DNA of the mould,
   while during the transformation of the mould the presence of the rare-cutting endonuclease is provided,
   (iii) selecting or screening for a mould cell in which the multiple gene copies of said expressible gene are inserted into the chromosomal DNA of the mould.

2. A process according to claim 1, in which the rare-cutting endonuclease is I-SceI.

3. A process according to claim 1, in which the restriction site for the rare-cutting endonuclease has been introduced at a desired locus.

4. A process according to claim 1, in which the restriction site for the rare-cutting endonuclease occurs naturally in the chromosomal DNA of the mould.

5. A process according to claim 1, in which two or more restriction sites for the rare-cutting endonuclease are present in the chromosomal DNA of the mould.

6. A process according claim 1, in which the expressible gene comprises (1) a promoter operable in said mold, (2) optionally a DNA fragment encoding a secretion signal peptide facilitating the secretion of said desired protein from said mould, (3) a structural gene encoding said desired protein, and (4) optionally a terminator operable in said mould, whereby 4 the promoter and the optional terminator control the expression of the structural gene.

7. A process according to claim 1, in which during the transformation of the mould the rare-cutting endonuclease is provided by adding the endonuclease as such, and/or is formed in situ by co-transforming the mould with DNA encoding the rare-cutting endonuclease which DNA is to be expressed during or after the transformation of the mould.

8. A process according to claim 1, in which the mould belongs to the group Eumycota.

9. A transformed mould obtained by the process of claim 1.

10. A process according to claim 3, in which the desired locus is within a selectable marker gene.

11. A process according to claim 10, in which the piece of DNA comprises a third DNA fragment that completes any disrupted or partially deleted selectable marker gene in the chromosomal DNA as to allow selection of strains containing the targeted integration by way of the selectable marker gene.

12. A process according to claim 10, which the part of the DNA up-stream of the restriction site for the rare-cutting endonuclease present in the chromosomal DNA of the mould, to which the first DNA fragment is homologous, is part of a selectable marker gene.

13. A process according to claim 10, in which the part of the DNA down-stream of tie restriction site for the rare-cutting endonuclease present in the chromosomal DNA of the mould, to which the second DNA fragment is homologous, is part of a selectable marker gene.

14. A process according to claim 8, in which the mould is selected from the genus Aspergillus.

15. The process according to claim 8, wherein said mold is further selected from the group consisting of the fungal subdivisions Ascomycotina, Basidiomycotina, Deuteromycotina, Mastigomycotina, and Zygomycotina.

16. The process according to claim 14, in which the mould belongs to the species *Aspergillus awamori*.

17. A process for producing a desired protein by carrying out a process wherein a mould according to claim 9, is cultured under conditions whereby the structural gene encoding said desired protein is expressed, and optionally isolating or concentrating the desired protein.

18. The process according to claim 17, wherein said gene comprises a DNA fragment encoding a secretion signal peptide facilitating the secretion of said desired protein from said mould.

* * * * *

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
tagggataac agggtaat                                                       18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
aattcatgcg gccgctagct                                                     20

<210> SEQ ID NO 3
```

```
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
gacaaggtcg ttgcgtcagt c                                              21

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
cgggatcctt ccatatgtga tgtctgctca agcgg                               35

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
gccagtacac tacttcttcg                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
aggagatcgc gagaaggttg                                                20
```